US011612447B2

(12) United States Patent
Limon et al.

(10) Patent No.: US 11,612,447 B2
(45) Date of Patent: Mar. 28, 2023

(54) MEDICAL DEVICES HAVING THREE TOOL MEMBERS

(71) Applicant: Intuitive Surgical Operations, Inc., Sunnyvale, CA (US)

(72) Inventors: Timothy A. Limon, Cupertino, CA (US); Grant Duque, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 695 days.

(21) Appl. No.: 16/513,105

(22) Filed: Jul. 16, 2019

(65) Prior Publication Data

US 2020/0022765 A1 Jan. 23, 2020

Related U.S. Application Data

(60) Provisional application No. 62/700,557, filed on Jul. 19, 2018.

(51) Int. Cl.
*A61B 34/00* (2016.01)
*A61B 34/30* (2016.01)
(Continued)

(52) U.S. Cl.
CPC .............. *A61B 34/70* (2016.02); *A61B 34/30* (2016.02); *A61B 34/71* (2016.02); *B25J 17/02* (2013.01);
(Continued)

(58) Field of Classification Search
CPC ......... A61B 34/30; A61B 34/70; A61B 34/71; A61B 2017/00367; A61B 2017/2938;
(Continued)

(56) References Cited

U.S. PATENT DOCUMENTS 2,214,985 A * 9/1940 Bachmann ......... A61B 17/2812
606/208
3,841,317 A 10/1974 Awais
(Continued)

FOREIGN PATENT DOCUMENTS

WO WO-2011161626 A2 12/2011
WO WO-2012068156 A2 5/2012
(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — Sarah A Simpson

(57) ABSTRACT

A medical device includes a link, a first tool member, a second tool member and a third tool member, which each have a proximal end portion movably coupled to the link and a distal end portion. The distal end portion of the first tool member can engage a first object and be associated with a first medical function, the distal end portion of the second tool member can engage a second object and be associated with a second medical function, and the distal end portion of the third tool member can engage the first object or the second object and be associated with the first and/or second medical function. Each of the first, second and third tool members can move relative to the link independent of movement of the each of the other tool members.

15 Claims, 21 Drawing Sheets

(51) Int. Cl.
*B25J 17/02* (2006.01)
*A61B 17/00* (2006.01)

(52) U.S. Cl.
CPC .............. *A61B 2017/00367* (2013.01); *A61B 2034/302* (2016.02); *A61B 2034/305* (2016.02)

(58) Field of Classification Search
CPC ......... A61B 2034/302; A61B 2034/305; B25J 17/02
See application file for complete search history.

(56) References Cited

U.S. PATENT DOCUMENTS

| | | |
|---|---|---|
| 5,052,402 A | 10/1991 | Bencini et al. |
| 5,318,589 A | 6/1994 | Lichtman |
| 5,373,854 A | 12/1994 | Kolozsi |
| 5,395,375 A | 3/1995 | Turkel et al. |
| 5,396,900 A | 3/1995 | Slater et al. |
| 5,476,479 A | 12/1995 | Green et al. |
| 5,482,054 A | 1/1996 | Slater et al. |
| 5,496,317 A | 3/1996 | Goble et al. |
| 5,496,347 A | 3/1996 | Hashiguchi et al. |
| 5,527,339 A | 6/1996 | Koscher et al. |
| 5,575,805 A | 11/1996 | Li |
| 5,582,617 A | 12/1996 | Klieman et al. |
| 5,601,575 A | 2/1997 | Measamer et al. |
| 5,722,935 A | 3/1998 | Christian |
| 5,792,135 A | 8/1998 | Madhani et al. |
| 5,792,165 A | 8/1998 | Klieman et al. |
| 5,855,583 A | 1/1999 | Wang et al. |
| 5,906,630 A | 5/1999 | Anderhub et al. |
| 5,968,074 A | 10/1999 | Prestel |
| 6,197,017 B1 | 3/2001 | Brock et al. |
| 6,206,903 B1 | 3/2001 | Ramans |
| 6,214,010 B1 | 4/2001 | Farley et al. |
| 6,273,860 B1 | 8/2001 | Kostylev et al. |
| 6,331,181 B1 | 12/2001 | Tierney et al. |
| 6,368,290 B1 | 4/2002 | Baska |
| 6,371,952 B1 | 4/2002 | Madhani et al. |
| 6,394,998 B1 | 5/2002 | Wallace et al. |
| 6,491,691 B1 | 12/2002 | Morley et al. |
| 6,554,844 B2 | 4/2003 | Lee et al. |
| 6,623,482 B2 | 9/2003 | Pendekanti et al. |
| 6,685,698 B2 | 2/2004 | Morley et al. |
| 6,767,349 B2 | 7/2004 | Ouchi |
| 6,817,974 B2 | 11/2004 | Cooper et al. |
| 6,840,938 B1 | 1/2005 | Morley et al. |
| 6,843,793 B2 | 1/2005 | Brock et al. |
| 6,949,106 B2 | 9/2005 | Brock et al. |
| 6,994,708 B2 | 2/2006 | Manzo et al. |
| 7,083,571 B2 | 8/2006 | Wang et al. |
| 7,090,683 B2 | 8/2006 | Brock et al. |
| 7,147,650 B2 | 12/2006 | Lee |
| 7,169,141 B2 | 1/2007 | Brock et al. |
| 7,214,230 B2 | 5/2007 | Brock et al. |
| 7,338,513 B2 | 3/2008 | Lee et al. |
| 7,371,210 B2 | 5/2008 | Brock et al. |
| 7,608,083 B2 | 10/2009 | Lee et al. |
| 7,824,401 B2 | 11/2010 | Manzo et al. |
| 7,935,130 B2 | 5/2011 | Williams et al. |
| 8,257,371 B2 | 9/2012 | Hamilton et al. |
| 8,479,969 B2 | 7/2013 | Shelton, IV et al. |
| 8,540,748 B2 | 9/2013 | Murphy et al. |
| 8,602,288 B2 | 12/2013 | Shelton, IV et al. |
| 8,771,270 B2 | 7/2014 | Burbank et al. |
| 8,800,838 B2 | 8/2014 | Shelton, IV et al. |
| 9,028,494 B2 | 5/2015 | Shelton, IV et al. |
| 9,078,684 B2 | 7/2015 | Williams et al. |
| 9,204,923 B2 | 12/2015 | Manzo et al. |
| 9,339,341 B2 | 5/2016 | Cooper |
| 9,358,031 B2 | 6/2016 | Manzo et al. |
| 9,456,839 B2 | 10/2016 | Cooper et al. |
| 9,554,790 B2 | 1/2017 | Bailey et al. |
| 9,615,846 B2 | 4/2017 | Prestel |
| 9,918,731 B2 | 3/2018 | Cooper et al. |
| 10,130,366 B2 | 11/2018 | Shelton, IV et al. |
| 10,667,873 B2 | 6/2020 | Wallace |
| 10,905,411 B2 * | 2/2021 | Racenet ............ A61B 17/0469 |
| 2004/0260198 A1 | 12/2004 | Rothberg et al. |
| 2005/0187547 A1 | 8/2005 | Sugi |
| 2005/0192598 A1 | 9/2005 | Johnson et al. |
| 2006/0074415 A1 | 4/2006 | Scott et al. |
| 2006/0184198 A1 | 8/2006 | Bales et al. |
| 2006/0190034 A1 | 8/2006 | Nishizawa et al. |
| 2007/0208375 A1 | 9/2007 | Nishizawa et al. |
| 2008/0046122 A1 | 2/2008 | Manzo et al. |
| 2008/0065102 A1 | 3/2008 | Cooper et al. |
| 2008/0065105 A1 | 3/2008 | Larkin et al. |
| 2008/0125794 A1 | 5/2008 | Brock et al. |
| 2008/0196533 A1 | 8/2008 | Bergamasco et al. |
| 2009/0088774 A1 | 4/2009 | Swarup et al. |
| 2009/0110533 A1 | 4/2009 | Jinno et al. |
| 2009/0131975 A1 | 5/2009 | Ahlberg et al. |
| 2009/0198272 A1 | 8/2009 | Kerver et al. |
| 2009/0326530 A1 | 12/2009 | Orban, III et al. |
| 2010/0030238 A1 | 2/2010 | Viola et al. |
| 2011/0276085 A1 | 11/2011 | Krzyzanowski et al. |
| 2011/0295269 A1 | 12/2011 | Swensgard et al. |
| 2011/0295270 A1 | 12/2011 | Giordano et al. |
| 2012/0116433 A1 | 5/2012 | Houser et al. |
| 2012/0289975 A1 | 11/2012 | Martin et al. |
| 2013/0144395 A1 | 6/2013 | Stefanchik et al. |
| 2014/0005662 A1 | 1/2014 | Shelton, IV |
| 2014/0005678 A1 | 1/2014 | Shelton, IV et al. |
| 2014/0005708 A1 | 1/2014 | Shelton, IV |
| 2014/0073856 A1 | 3/2014 | Stein et al. |
| 2014/0100558 A1 | 4/2014 | Schmitz et al. |
| 2014/0243850 A1 | 8/2014 | Sadaka |
| 2014/0276956 A1 | 9/2014 | Crainich et al. |
| 2015/0150584 A1 * | 6/2015 | Van Tol ............... A61B 17/295<br>606/51 |
| 2015/0150635 A1 * | 6/2015 | Kilroy .................... A61B 34/30<br>606/130 |
| 2015/0157355 A1 | 6/2015 | Price et al. |
| 2015/0313676 A1 | 11/2015 | Deodhar |
| 2016/0287279 A1 | 10/2016 | Bovay et al. |
| 2016/0296219 A1 | 10/2016 | Srivastava et al. |
| 2016/0303743 A1 | 10/2016 | Rockrohr et al. |
| 2017/0165017 A1 | 6/2017 | Chaplin et al. |
| 2017/0252096 A1 | 9/2017 | Felder et al. |
| 2017/0333037 A1 | 11/2017 | Wellman et al. |
| 2018/0168572 A1 | 6/2018 | Burbank |
| 2018/0206904 A1 | 7/2018 | Felder et al. |
| 2019/0099227 A1 | 4/2019 | Rockrohr |
| 2019/0192137 A1 | 6/2019 | Shelton, IV et al. |
| 2019/0223960 A1 | 7/2019 | Chaplin et al. |
| 2019/0231374 A1 | 8/2019 | Kimura et al. |
| 2019/0374297 A1 | 12/2019 | Wallace et al. |
| 2020/0015807 A1 | 1/2020 | Limon et al. |
| 2020/0054405 A1 | 2/2020 | Schuh et al. |
| 2020/0054408 A1 | 2/2020 | Schuh et al. |
| 2020/0138531 A1 | 5/2020 | Chaplin |
| 2020/0155136 A1 | 5/2020 | Shuh et al. |
| 2020/0155253 A1 | 5/2020 | Shuh et al. |

FOREIGN PATENT DOCUMENTS

| | | |
|---|---|---|
| WO | WO-2014025204 A1 | 2/2014 |
| WO | WO-2016025132 A1 | 2/2016 |
| WO | WO-2016045041 A1 | 3/2016 |
| WO | WO-2016123139 A2 | 8/2016 |
| WO | WO-2017064303 A1 | 4/2017 |
| WO | WO-2017189272 A1 | 11/2017 |
| WO | WO-2018069679 A1 | 4/2018 |
| WO | WO-2022072732 A1 | 4/2022 |

* cited by examiner

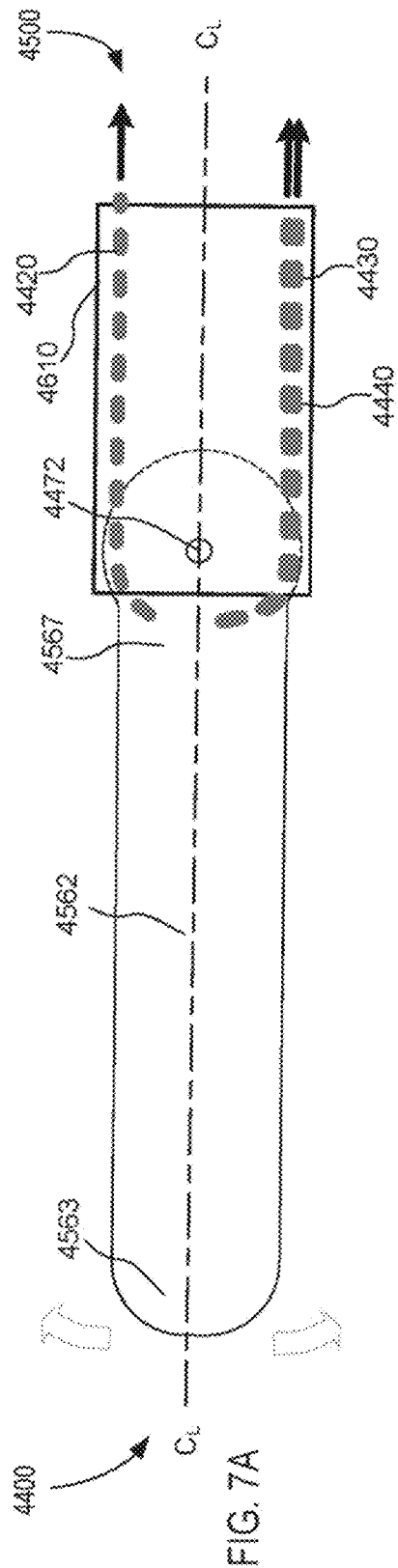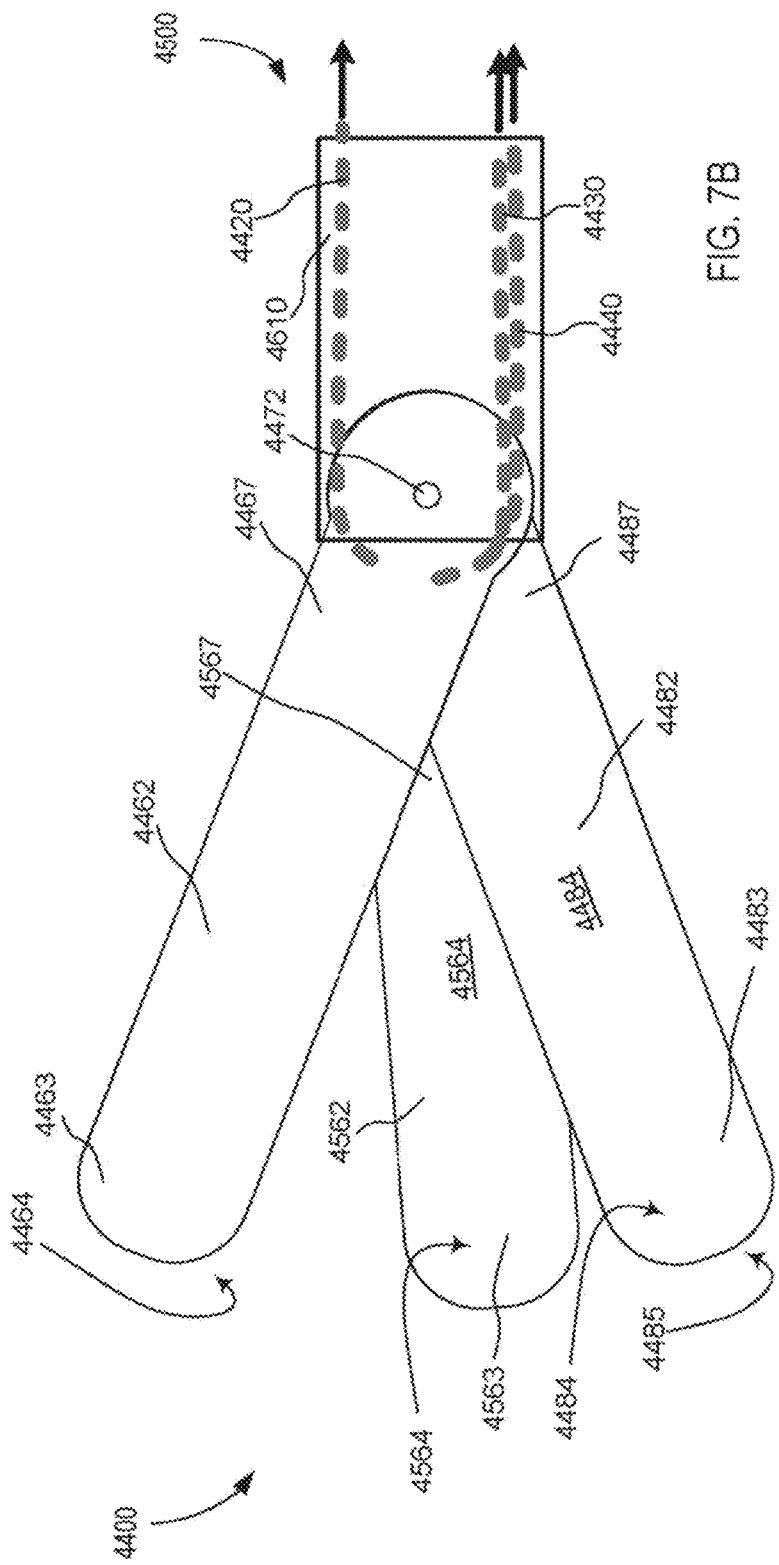

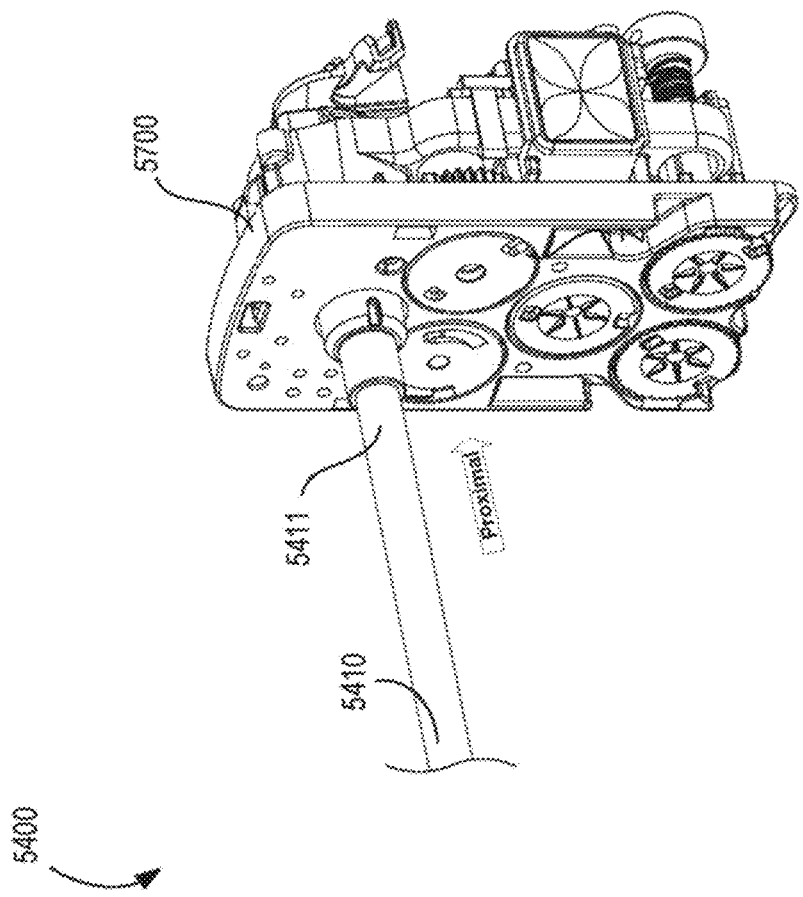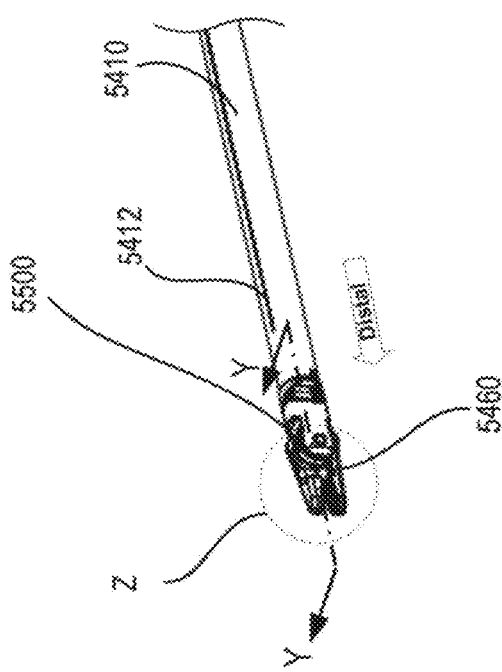
FIG. 8A

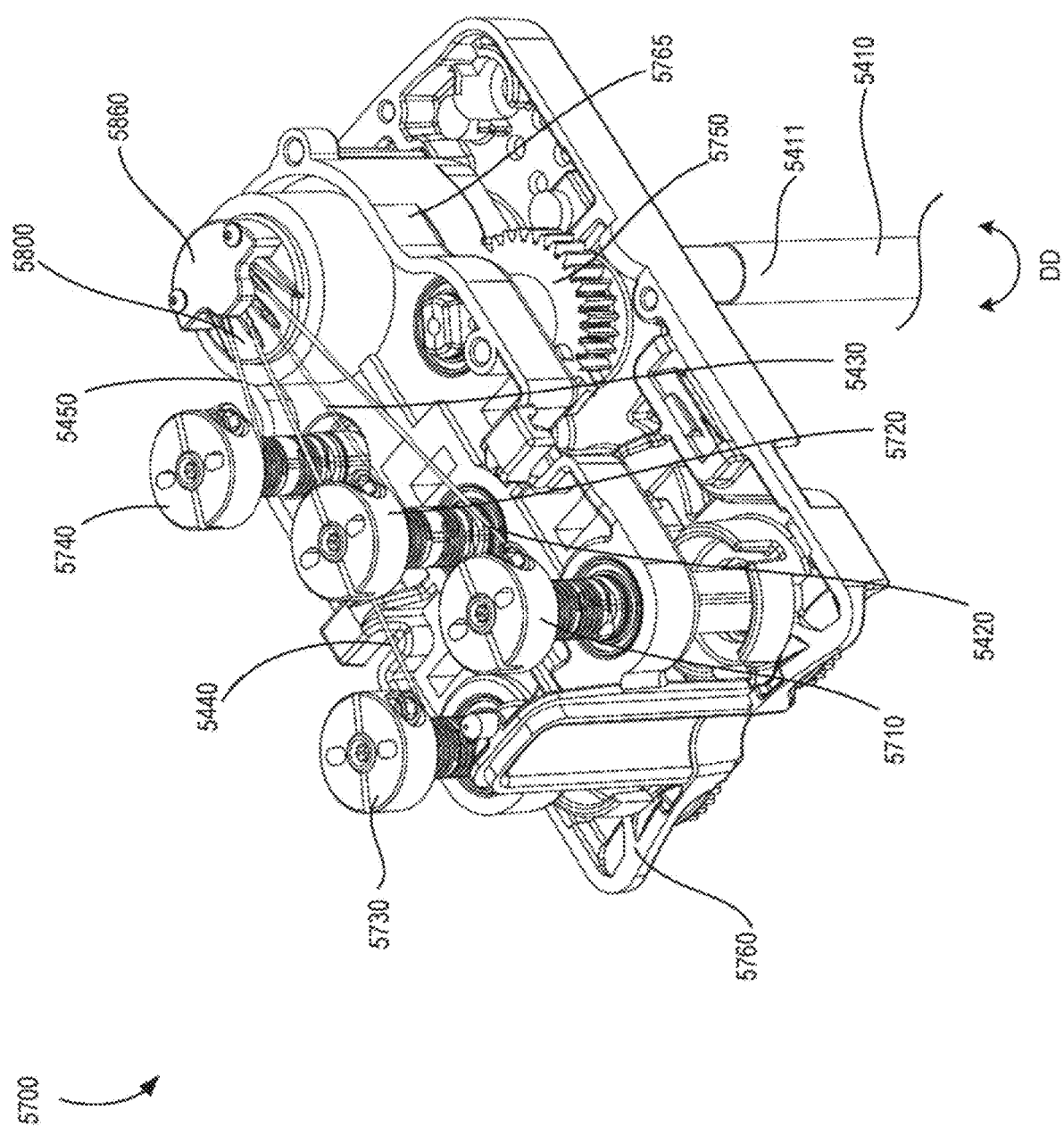

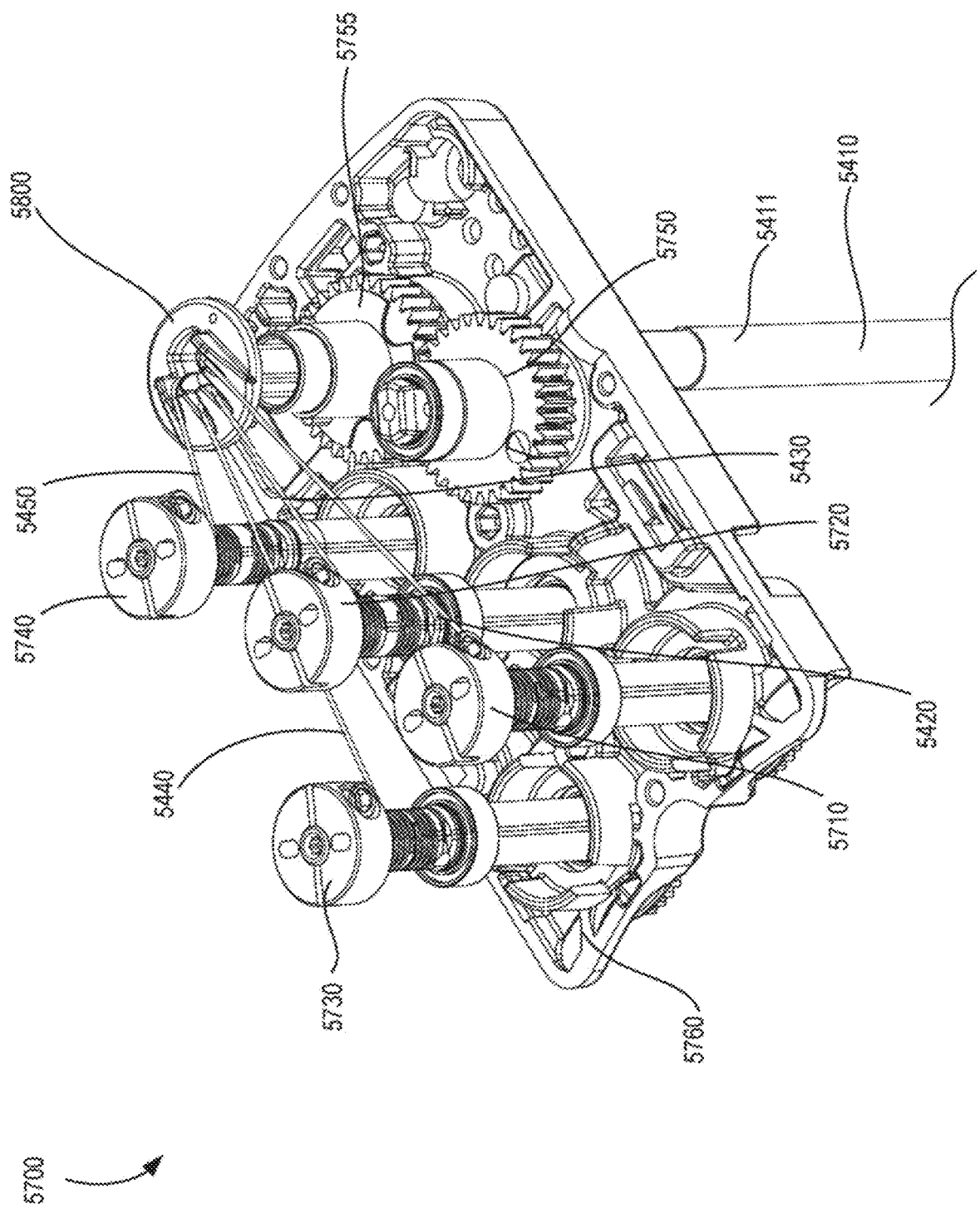

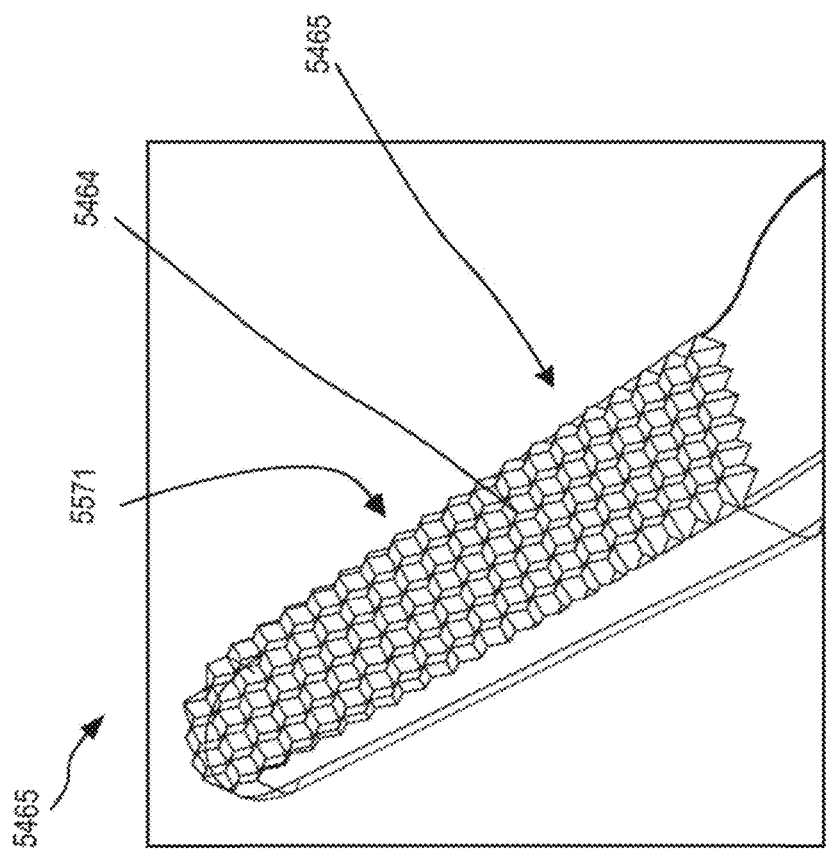
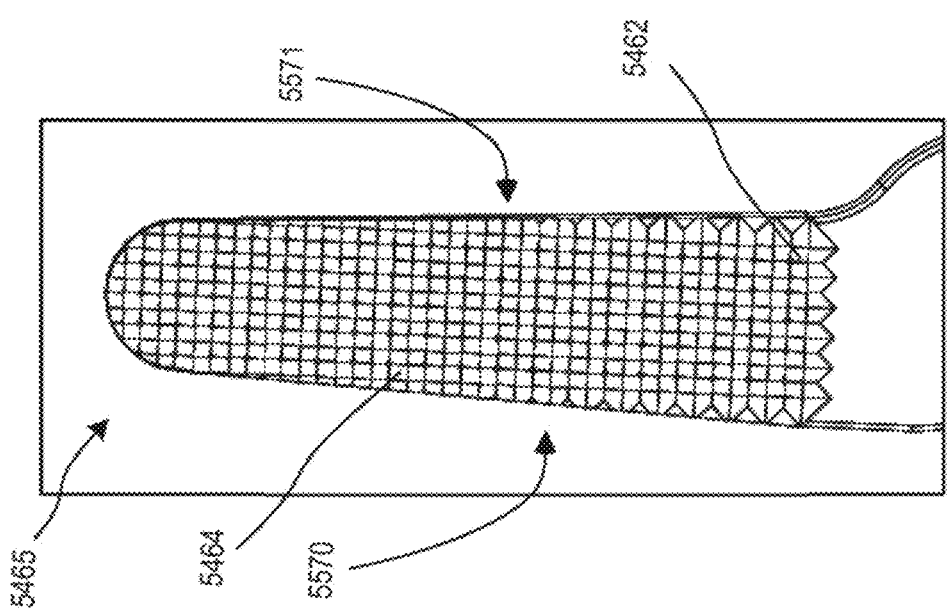
FIG. 14B
FIG. 14A

MEDICAL DEVICES HAVING THREE TOOL MEMBERS

CROSS-REFERENCE TO RELATED APPLICATIONS

This patent application claims priority to and the filing date benefit of U.S. Provisional Application No. 62/700,557 (filed Jul. 19, 2018) (entitled "Medical Devices Having Three Tool Members"), which is incorporated herein by reference in its entirety.

BACKGROUND

The embodiments described herein relate to grasping tools, more specifically to medical devices, and still more specifically to endoscopic tools. More particularly, the embodiments described herein relate to articulable medical devices that include multi-functional instruments including instruments having three or more tool members that can be used, for example, in surgical applications.

Known techniques for Minimally Invasive Surgery (MIS) employ instruments to manipulate tissue that can be either manually controlled or controlled via computer-assisted teleoperation. Many known MIS instruments include a therapeutic or diagnostic end effector (e.g., forceps, a cutting tool, or a cauterizing tool) mounted on a wrist mechanism at the distal end of an extension (also referred to herein as the main tube or shaft). During an MIS procedure, the end effector, wrist mechanism, and the distal end of the main tube can be inserted into a small incision or a natural orifice of a patient to position the end effector at a work site within the patient's body. The optional wrist mechanism can be used to change the end effector's orientation with respect to the main tube to perform the desired procedure at the work site. Known wrist mechanisms generally provide the desired degrees of freedom (DOFs) for movement of the end effector. For example, for forceps or other grasping tools, known wrist mechanisms are often able to change the pitch and yaw of the end effector with reference to the main tube. A wrist may optionally provide a roll DOF for the end effector, or the roll DOF may be implemented by rolling the main tube. An end effector may optionally have additional mechanical DOFs, such as grip or knife blade motion. In some instances, wrist and end effector mechanical DOFs may be combined. For example, U.S. Pat. No. 5,792,135 (filed May 16, 1997) discloses a mechanism in which wrist and end effector grip DOFs are combined.

Many different MIS tools, including tools designed for specific clinical functions, are used during each medical procedure to perform functions such as desiccation, hemostasis, cutting, dissection, fulguration, incisions, tissue destruction, cauterizing, vessel sealing, and imaging. In order to meet size requirements, conventional end effectors of articulable MIS instruments include either a single tool member or a pair of cooperating tool members that are customized for particular clinical functions, such as a single tool for making incisions or a pair of jaws for grasping and manipulating tissue. Accordingly, various different MIS instruments are interchanged during medical procedures to perform clinical functions throughout the procedure, such as switching between instruments for making incisions, obtaining biopsies, manipulating and removing tissue, cauterizing or sealing blood vessels, and stitching tissues. Adding and removing medical instruments during a procedure can create challenges including maintaining a sterile environment and minimizing the length of the procedure, which can be reduced through the use of multi-functional instruments. However, it can be challenging to provide multi-functional MIS clinical instruments without increasing the tool diameter or limiting degrees of freedom of the instrument. Further, it can be challenging to incorporate additional tool members in an articulable MIS instrument to expand its clinical functionality while preserving component interoperability and supporting drive forces for their desired operability.

Thus, a need exists for improved endoscopic tools and multi-functional endoscopic tools. Improvements may include articulable instruments having three or more tool members for performing multiple clinical functions while maintaining small instrument diameters and desired functional operability of its components.

SUMMARY

This summary introduces certain aspects of the embodiments described herein to provide a basic understanding. This summary is not an extensive overview of the inventive subject matter, and it is not intended to identify key or critical elements or to delineate the scope of the inventive subject matter.

In some embodiments, an apparatus includes a link, a first tool member, a second tool member, and a third tool member. Each of the tool members has a proximal end portion movably coupled to the link and a distal end portion. The first tool member distal end portion is configured to engage a first object, the second tool member distal end portion is configured to engage a second object, and the third tool member distal end portion is configured to engage at least one of the first object or the second object. The first tool member is configured to move relative to the link independent of movement of the second tool member and the third tool member. The second tool member is configured to move relative to the link independent of movement of the first tool member and the third tool member. The third tool member is configured to move relative to the link independent of movement of the first tool member and the second tool member. The first tool member, the second tool member, and the third tool member can each be configured to rotate relative to the link. Further, the link can be a distal clevis of a wrist assembly, in which the distal clevis includes a pin about which at least two of the first tool member, the second tool member, and the third tool member rotate.

In some embodiments, the first tool member proximal end portion is coupled to a first tension member, and the first tool member is movable relative to the link when the first tension member is moved. The second tool member proximal end portion is coupled to a second tension member, and the second tool member is movable relative to the link when the second tension member is moved. The third tool member proximal end portion is coupled to a third tension member, and the third tool member is movable relative to the link when the third tension member is moved. In some embodiments, the second tool member is between the first tool member and the third tool member. In some embodiments, the distal end portion of the first tool member has a first contact surface, the distal end portion of the second tool member has second contact surface and a fourth contact surface, and the distal end portion of the third tool member has a third contact surface. The first contact surface and the second contact surface are configured to manipulate the first object, and the third contact surface and the fourth contact surface are configured to manipulate the second object. In some embodiments, the first contact surface and the second contact surface have a first grip pattern, and the third contact surface and the fourth contact surface have a second grip pattern. The first grip pattern can be different from the second grip pattern. In some embodiments, the first object is different from the second object. In some embodiments, the first object is the same as the second object. In some embodiments, the first object and the second object include a target tissue.

In some embodiments, an apparatus includes a link, a first tool member, a second tool member, and a third tool member. The first tool member is coupled to the link and has a first contact surface with a first grip pattern. The second tool member is movably coupled to the link. The second tool member is coupled to the link and has a second contact surface with the first grip pattern and a fourth contact surface with a second grip pattern different from the first grip pattern.

In some embodiments, the second contact surface is on a first side of the second tool member. The second contact surface is aligned with the first contact surface when the first contact surface and the second contact surface manipulate a first object. The fourth contact surface is on a second side of the second tool member. The fourth contact surface is aligned with the third contact surface, and the second grip pattern on the third and fourth contact surfaces are aligned with each other when the third contact surface and the fourth contact surface manipulate a second object. The second tool member can be between the first tool member and the third tool member. The first tool member, the second tool member, and the third tool member can each be configured to rotate relative to the link.

In some embodiments, an apparatus includes a clevis, a pin coupled to the clevis, a first tool member, a second tool member, and a third tool member. The first tool member is rotatably coupled to the clevis to rotate about the pin, and the first tool member defines a first blade having a first elongate body. The second tool member is rotatably coupled to the clevis to rotate about the pin, and the second tool member defines a second blade having a second elongate body. The third tool member is rotatably coupled to the clevis to rotate about the pin. The third tool member defines a third blade having a third elongate body. The first tool member is configured to rotate relative to the clevis independent of the second tool member and the third tool member. The second tool member is configured to rotate relative to the clevis independent of movement of the first tool member and the third tool member. The third tool member is configured to rotate relative to the clevis independent of movement of the first tool member and the second tool member. Each of the first, second and third tool members are configured to rotate parallel to each other without making interfering contact between another one of the first, second and third tool members.

In some embodiments, a medical device includes a first clevis assembly including a first clevis pin, a first jaw piece, a second jaw piece, and a third jaw piece. The first jaw piece includes a portion associated with a first medical function. The second jaw piece includes an obverse portion associated with a first medical function and a reverse portion associated with a second medical function. The third jaw piece includes a portion associated with the second medical function. The first jaw piece, the second jaw piece and the third jaw piece rotate around the first clevis pin. The portion of the first jaw piece associated with the first medical function opposes the obverse portion of the second jaw piece associated with the first medical function. The portion of the second jaw piece associated with the second medical function opposes the reverse portion of the second jaw piece associated with the second medical function.

In some embodiments, the medical device can further include an instrument shaft comprising a distal end. The first clevis assembly can be coupled to the distal end of the instrument shaft. In some embodiments, the medical device can further include a second clevis assembly including a second clevis pin. The second clevis assembly can be coupled to the distal end of the instrument shaft, and the first clevis assembly can rotate around the second clevis pin. In some embodiments, the medical device can further include a first actuating member coupled to the first jaw piece, a second actuating member coupled to the second jaw piece, and a third actuating member coupled to the third jaw piece. The first, second, and third actuating members can extend proximally through the instrument shaft. In some embodiments, the medical device can further include a transmission assembly including a plurality of drive components, the transmission shaft can include a proximal end, the transmission assembly can be coupled to the proximal end of the instrument shaft, and the first, second and third actuating members can each be coupled to a corresponding one of the plurality of drive components of the transmission assembly. In some embodiments, the first medical function can include gripping tissue, retracting tissue, shearing tissue, ultrasonically cutting tissue, electrosurgically cauterizing tissue, electrosurgically sealing tissue, applying a clip to tissue, applying a staple to tissue, and/or grasping a needle. In some embodiments, the second medical can function can be different from the first medical function.

In some embodiments, a medical device includes a first jaw piece including a portion associated with a first medical function, a second jaw piece, and a third jaw piece including a portion associated with a second medical function. The second jaw piece includes an obverse portion associated with the first medical function and a reverse portion associated with the second medical function. The first and second jaw pieces are movably coupled such that the portion of the first jaw piece associated with the first medical function and the obverse portion of the second jaw piece associated with the first medical function close together. The third and second jaw pieces are movably coupled such that the portion of the third jaw piece associated with the second medical function and the reverse portion of the second jaw piece associated with the second medical function close together.

In some embodiments, the medical device can further include an instrument shaft including a proximal end and a distal end, an actuating member, and a transmission mechanism including a drive component. The first, the second, and the third jaw pieces can be located at the distal end of the instrument shaft. The transmission mechanism can be coupled to the proximal end of the instrument shaft. The actuating member can be coupled to one of the first, second, or third jaw pieces, can extend proximally through the instrument shaft, and can be coupled to the drive component. In some embodiments, one of the first or second jaw members can be fixed with reference to the instrument shaft.

Other medical devices, related components, medical device systems, and/or methods according to embodiments will be or become apparent to one with skill in the art upon review of the following drawings and detailed description. It is intended that all such additional medical devices, related components, medical device systems, and/or methods included within this description be within the scope of this disclosure.

BRIEF DESCRIPTION OF THE DRAWINGS

FIG. 7A is a diagrammatic side view of an instrument of a surgery system in a first orientation, according to an embodiment.

FIG. 7B is a diagrammatic side view of the instrument of a surgery system of FIG. 7A shown in a second orientation.

FIG. 8A is a perspective view of an instrument of a surgery system in a first orientation, according to an embodiment.

FIGS. 8B and 8C are enlarged perspective views of a transmission at the proximal end portion of the instrument shown in FIG. 8A.

FIG. 14A is a front view of the first gripping portion of the first tool member and the first grip pattern of the instrument of FIG. 8A, viewed from line C-C shown in FIG. 10.

FIG. 14B is a perspective view of the first gripping portion of the first tool member and the first grip pattern of the instrument of FIG. 8A.

DETAILED DESCRIPTION

Figure 1:
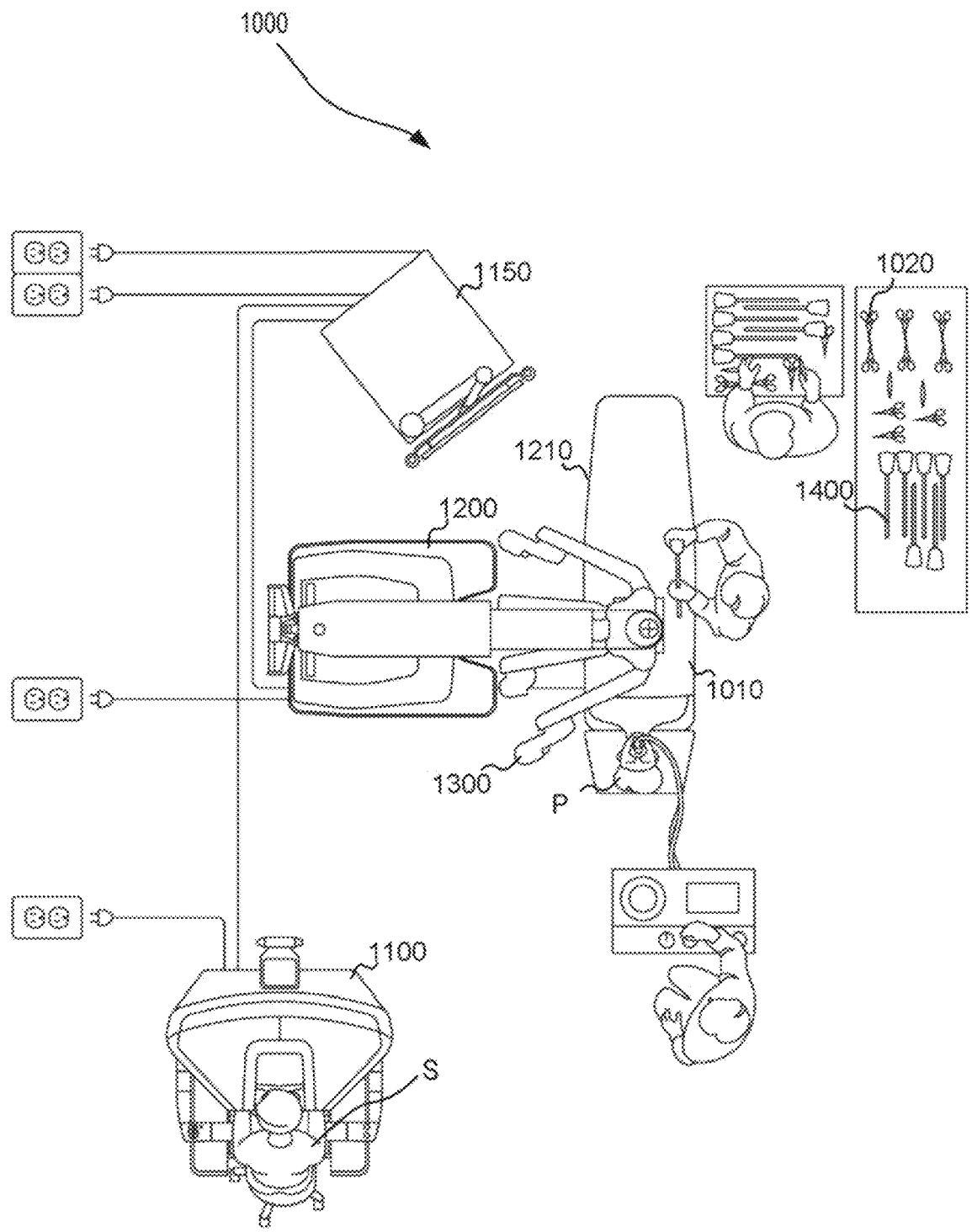
FIG. 1 is a plan view of a minimally invasive teleoperated medical system according to an embodiment, being used to perform a medical procedure such as surgery.

The embodiments described herein can advantageously be used in a wide variety of grasping, cutting, and manipulating operations associated with minimally invasive surgery. In particular, the instruments described herein can be low-cost, disposable instruments that facilitate being used for only one procedure. Furthermore, instruments described herein can be multi-functional MIS instruments configured to multiple combinations of clinical functions that are each performed by single MIS instruments, and can do so without requiring larger incisions or cannula diameters than the single MIS instruments. In addition, multi-functional instruments described herein can be configured to perform the various combinations of multiple clinical functions without loss of operability, maneuverability, or clinical functionality compared with corresponding single MIS instruments that would be required to provide the same functionality. As described herein, the multi-functional instruments can be driven by various drive components, such as combinations of motors, gears, actuators, transmission members, etc. Further, the multi-functional instruments described herein can include one or more cables (which act as tension members) that can be moved to actuate the end effector of a multi-functional MIS instrument to perform the various clinical functions and move with multiple degrees of freedom.

As used herein, the term "about" when used in connection with a referenced numeric indication means the referenced numeric indication plus or minus up to 10 percent of that referenced numeric indication. For example, the language "about 50" covers the range of 45 to 55. Similarly, the language "about 5" covers the range of 4.5 to 5.5.

As used herein, the term "target workspace" refers to anything within or pertaining to the endoscopic work cavity including the body of the patient, P, tissues and organs within the cavity, and tissue defining the cavity, and also to support structures for the MIS procedure including a cover and cannula supports, instruments and related attachments or medical implements including needles, suture materials, implants, meshes, etc. As used herein, the term "target tissue" refers to any tissue or organ that interacts with the target workspace including tissues and organs of the patient, P, natural tissues and organs introduced to the target workspace including natural transplant tissues and organs, artificial tissues and organs including mechanical or electromechanical organs, and tissue and organ assist devices such as pacemakers, mesh material, artificial skin and the like.

The term "flexible" in association with a part, such as a mechanical structure, component, or component assembly, should be broadly construed. In essence, the term means the part can be repeatedly bent and restored to an original shape without harm to the part. Certain flexible components can also be resilient. For example, a component (e.g., a flexure) is said to be resilient if possesses the ability to absorb energy when it is deformed elastically, and then release the stored energy upon unloading (i.e., returning to its original state).

Many "rigid" objects have a slight inherent resilient "bendiness" due to material properties, although such objects are not considered "flexible" as the term is used herein.

A flexible part may have infinite degrees of freedom (DOF's). Flexibility is an extensive property of the object being described, and thus is dependent upon the material from which the object is formed as well as certain physical characteristics of the object (e.g., cross-sectional shape, length, boundary conditions, etc.). For example, the flexibility of an object can be increased or decreased by selectively including in the object a material having a desired modulus of elasticity, flexural modulus, and/or hardness. The modulus of elasticity is an intensive property of (i.e., is intrinsic to) the constituent material and describes an object's tendency to elastically (i.e., non-permanently) deform in response to an applied force. A material having a high modulus of elasticity will not deflect as much as a material having a low modulus of elasticity in the presence of an equally applied stress. Thus, the flexibility of the object can be decreased, for example, by introducing into the object and/or constructing the object of a material having a relatively high modulus of elasticity. Examples of such parts include closed, bendable tubes (made from, e.g., NITINOL®, polymer, soft rubber, and the like), helical coil springs, etc. that can be bent into various simple or compound curves, often without significant cross-sectional deformation.

Other flexible parts may approximate such an infinite-DOF part by using a series of closely spaced components that are similar to a serial arrangement of short, connected links as snake-like "vertebrae." In such a vertebral arrangement, each component is a short link in a kinematic chain, and movable mechanical constraints (e.g., pin hinge, cup and ball, live hinge, and the like) between each link may allow one (e.g., pitch) or two (e.g., pitch and yaw) DOFs of relative movement between the links. A short, flexible part may serve as, and be modeled as, a single mechanical constraint (a joint) that provides one or more DOF's between two links in a kinematic chain, even though the flexible part itself may be a kinematic chain made of several coupled links having multiple DOFs, or an infinite-DOF link.

As used in this specification and the appended claims, the word "distal" refers to direction towards a work site, and the word "proximal" refers to a direction away from the work site. Thus, for example, the end of a tool that is closest to the target tissue would be the distal end of the tool, and the end opposite the distal end (i.e., the end manipulated by the user or coupled to the actuation shaft) would be the proximal end of the tool.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe the relationship of one element or feature to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures were turned over, elements described as "below" or "beneath" other elements or features would then be "above" or "over" the other elements or features. Thus, the term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various spatial device positions and orientations. The combination of a body's position and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

In addition, as used in the specification and in the appended claims, the word "obverse" refers to the counterpart of what it references, which can mean the opposite or other side of the reference without limitation. With respect to aspects and features described herein, the term obverse indicates a corresponding aspect or feature without limitation to a specific orientation, alignment the corresponding references, or to a preferred orientation or arrangement. For example, features of a component such as a jaw or other tool member can be described herein in various ways for many different reasons, for which one reference could be identified as 'obverse' and a corresponding reference identified as 'reverse' for some descriptions and the opposite for other descriptions. The descriptions can vary, for instance, according to a manner that components correspond with drawing views, according to how the component is assembled within a device, and/or based on numerous other options like movements, operations, materials, particular functions performed, orientations shown in the various figures, etc.

The descriptions of corresponding aspects or features can arbitrarily denote the same as 'obverse' and 'reverse' without limitation as to whether one or the other corresponding thing is primary or secondary or whether one is intended to have a particular orientation vs. the other, such as forward facing or rearward facing. In addition, even though the terms "obverse" and "reverse" identify the references as corresponding to one or another, such correspondence is without specific limitations. For instance, a first face of a jaw or tool member can be described herein as an 'obverse' face, and a second face of a jaw or tool member can be described herein as a 'reverse' face of the tool member without implying limitations. For instance, the first face can be oriented along another non-parallel plane of the jaw or tool member, the first and second faces can have differing surface features or shapes, and can be formed from different materials. Nonetheless, it can be beneficial to refer to the faces as corresponding features according to the description, such that one is 'obverse' and the other 'reverse.'

In addition, the singular forms "a", "an", and "the" are intended to include the plural forms as well, unless the context indicates otherwise. The terms "comprises", "includes", "has", and the like specify the presence of stated features, steps, operations, elements, components, etc. but do not preclude the presence or addition of one or more other features, steps, operations, elements, components, or groups.

Unless indicated otherwise, the terms apparatus, medical device, instrument, and variants thereof, can be interchangeably used.

Aspects of the invention are described primarily in terms of an implementation using a da Vinci® Surgical System, commercialized by Intuitive Surgical, Inc. of Sunnyvale, Calif. Examples of such surgical systems are the da Vinci Xi® Surgical System (Model IS4000) and the da Vinci Si® Surgical System (Model IS3000). Knowledgeable persons will understand, however, that inventive aspects disclosed herein may be embodied and implemented in various ways, including computer-assisted, non-computer-assisted, and hybrid combinations of manual and computer-assisted embodiments and implementations. Implementations on da Vinci® Surgical Systems (e.g., the Model IS4000, the Model IS3000, the Model IS2000, the Model IS1200) are merely presented as examples, and they are not to be considered as limiting the scope of the inventive aspects disclosed herein. As applicable, inventive aspects may be embodied and implemented in both relatively smaller, hand-held, hand-operated devices and relatively larger systems that have additional mechanical support.

FIG. 1 is a plan view illustration of a computer-assisted teleoperation system. Shown is a medical device, which is a Minimally Invasive Robotic Surgical (MIRS) system 1000 (also referred to herein as a minimally invasive teleoperated surgery system), used for performing a minimally invasive diagnostic or surgical procedure on a Patient P who is lying on an Operating table 1010. The system can have any number of components, such as a user control unit 1100 for use by a surgeon or other skilled clinician S during the procedure. The MIRS system 1000 can further include a manipulator unit 1200 (popularly referred to as a surgical robot), and an optional auxiliary equipment unit 1150. The manipulator unit 1200 can include an arm assembly 1300 and a tool assembly removably coupled to the arm assembly. The manipulator unit 1200 can manipulate at least one removably coupled tool assembly 1400 (also referred to herein as a "tool") through a minimally invasive incision in the body or natural orifice of the patient P while the surgeon S views the surgical site and controls movement of the tool 1400 through control unit 1100.

An image of the surgical site is obtained by an endoscope (not shown), such as a stereoscopic endoscope, which can be manipulated by the manipulator unit 1200 to orient the endoscope. The auxiliary equipment unit 1150 can be used to process the images of the surgical site for subsequent display to the Surgeon S through the user control unit 1100. The number of tools 1400 used at one time will generally depend on the diagnostic or surgical procedure and the space constraints within the operating room, among other factors. If it is necessary to change one or more of the instruments 1400 being used during a procedure, an assistant removes the instrument 1400 from the manipulator unit 1200 and replaces it with another instrument 1400 from a tray 1020 in the operating room. Although shown as being used with the instruments 1400, any of the instruments described herein can be used with the MIRS 1000.

Figure 2:
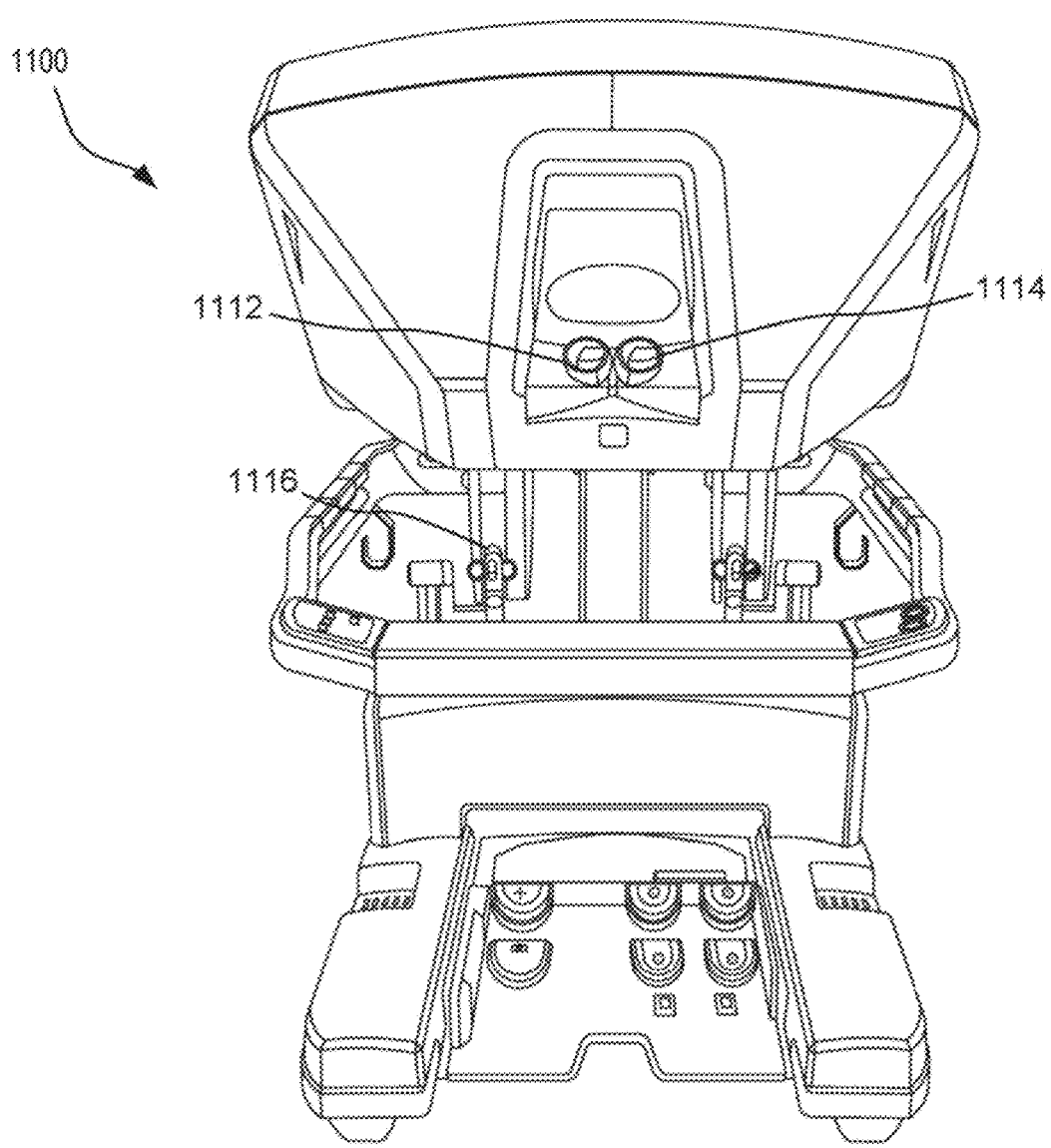
FIG. 2 is a perspective view of an optional auxiliary unit of the minimally invasive tele-operated surgery system shown in FIG. 1.

FIG. 2 is a perspective view of the control unit 1100. The user control unit 1100 includes a left eye display 1112 and a right eye display 1114 for presenting the surgeon S with a coordinated stereo view of the surgical site that enables depth perception. The user control unit 1100 further includes one or more input control devices 1116, which in turn cause the manipulator unit 1200 (shown in FIG. 1) to manipulate one or more tools. The input control devices 1116 provide at least the same degrees of freedom as instruments 1400 with which they are associated to provide the surgeon S with telepresence, or the perception that the input control devices 1116 are integral with (or are directly connected to) the instruments 1400. In this manner, the user control unit 1100 provides the surgeon S with a strong sense of directly controlling the instruments 1400. To this end, position, force, and tactile feedback sensors (not shown) may be employed to transmit position, force, and tactile sensations from the instruments 1400 back to the surgeon's hands through the input control devices 1116.

The user control unit 1100 is shown in FIG. 1 as being in the same room as the patient so that the surgeon S can directly monitor the procedure, be physically present if necessary, and speak to an assistant directly rather than over the telephone or other communication medium. In other embodiments however, the user control unit 1100 and the surgeon S can be in a different room, a completely different building, or other remote location from the patient allowing for remote surgical procedures.

Figure 3:
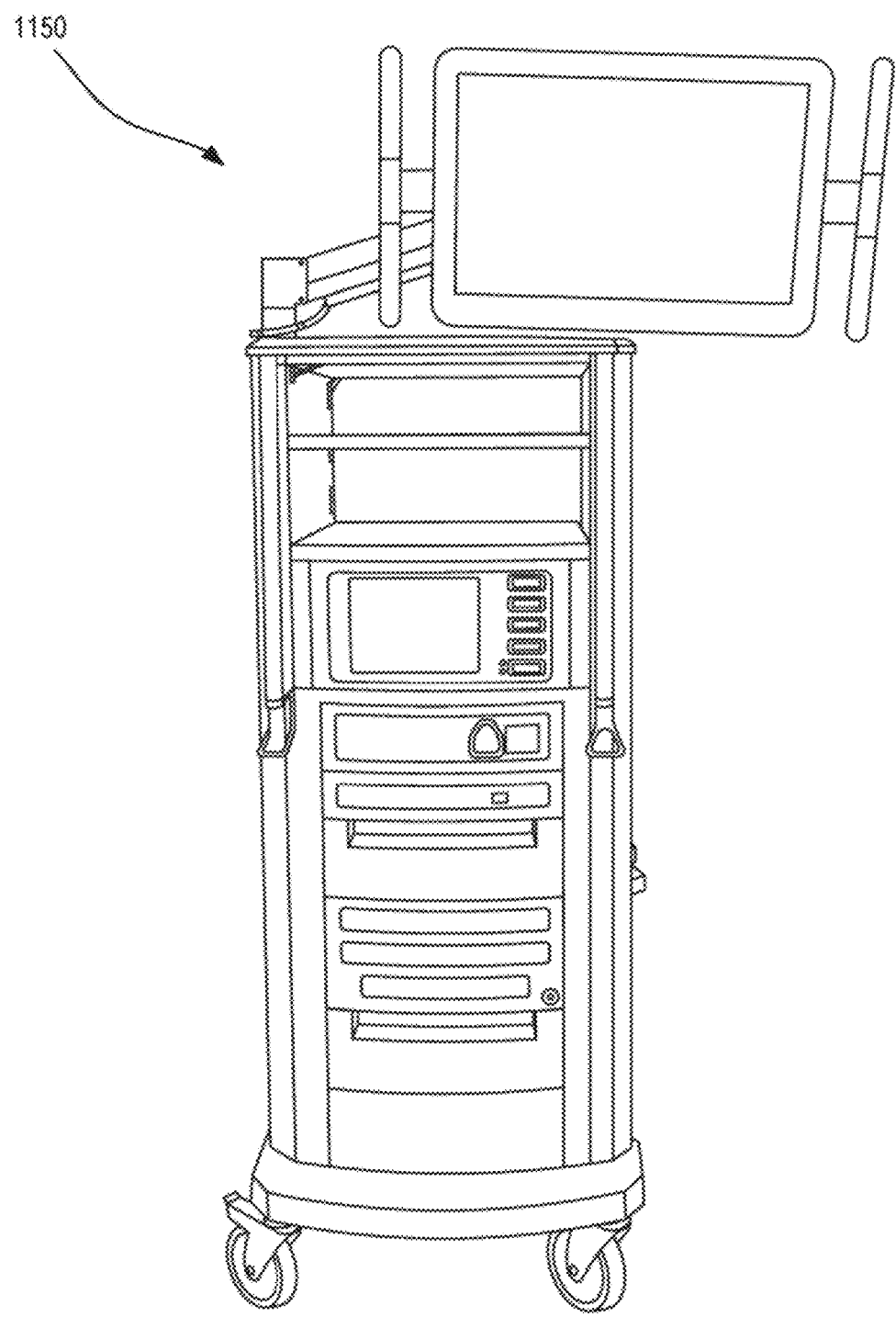
FIG. 3 is a perspective view of a user control console of the minimally invasive tele-operated surgery system shown in FIG. 1.

FIG. 3 is a perspective view of the auxiliary equipment unit 1150. The auxiliary equipment unit 1150 can be coupled with the endoscope (not shown) and can include one or more processors to process captured images for subsequent display, such as via the user control unit 1100, or on another suitable display located locally and/or remotely. For example, where a stereoscopic endoscope is used, the auxiliary equipment unit 1150 can process the captured images to present the surgeon S with coordinated stereo images of the surgical site via the left eye display 1112 and the right eye display 1114. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
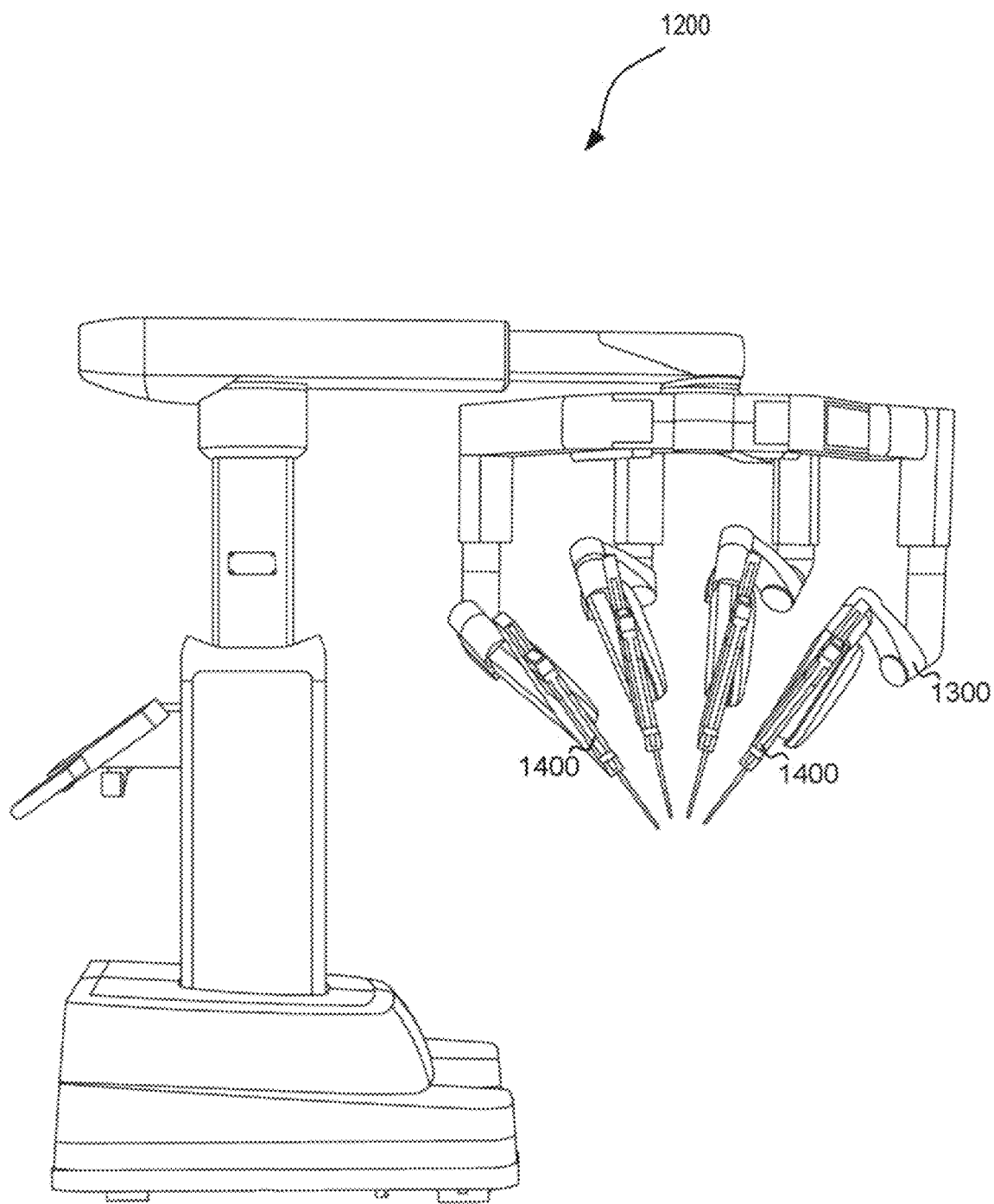
FIG. 4 is a front view of a manipulator unit, including a plurality of instruments, of the minimally invasive tele-operated surgery system shown in FIG. 1.

FIG. 4 shows a front perspective view of the manipulator unit 1200. The manipulator unit 1200 includes the components (e.g., arms, linkages, motors, sensors, and the like) to provide for the manipulation of the instruments 1400 and an imaging device (not shown), such as a stereoscopic endoscope, used for the capture of images of the site of the procedure. Specifically, the instruments 1400 and the imaging device can be manipulated by teleoperated mechanisms having a number of joints. Moreover, the instruments 1400 and the imaging device are positioned and manipulated through incisions or natural orifices in the patient P in a manner such that a kinematic remote center of motion is maintained at the incision or orifice. In this manner, the incision size can be minimized.

Figure 5A:
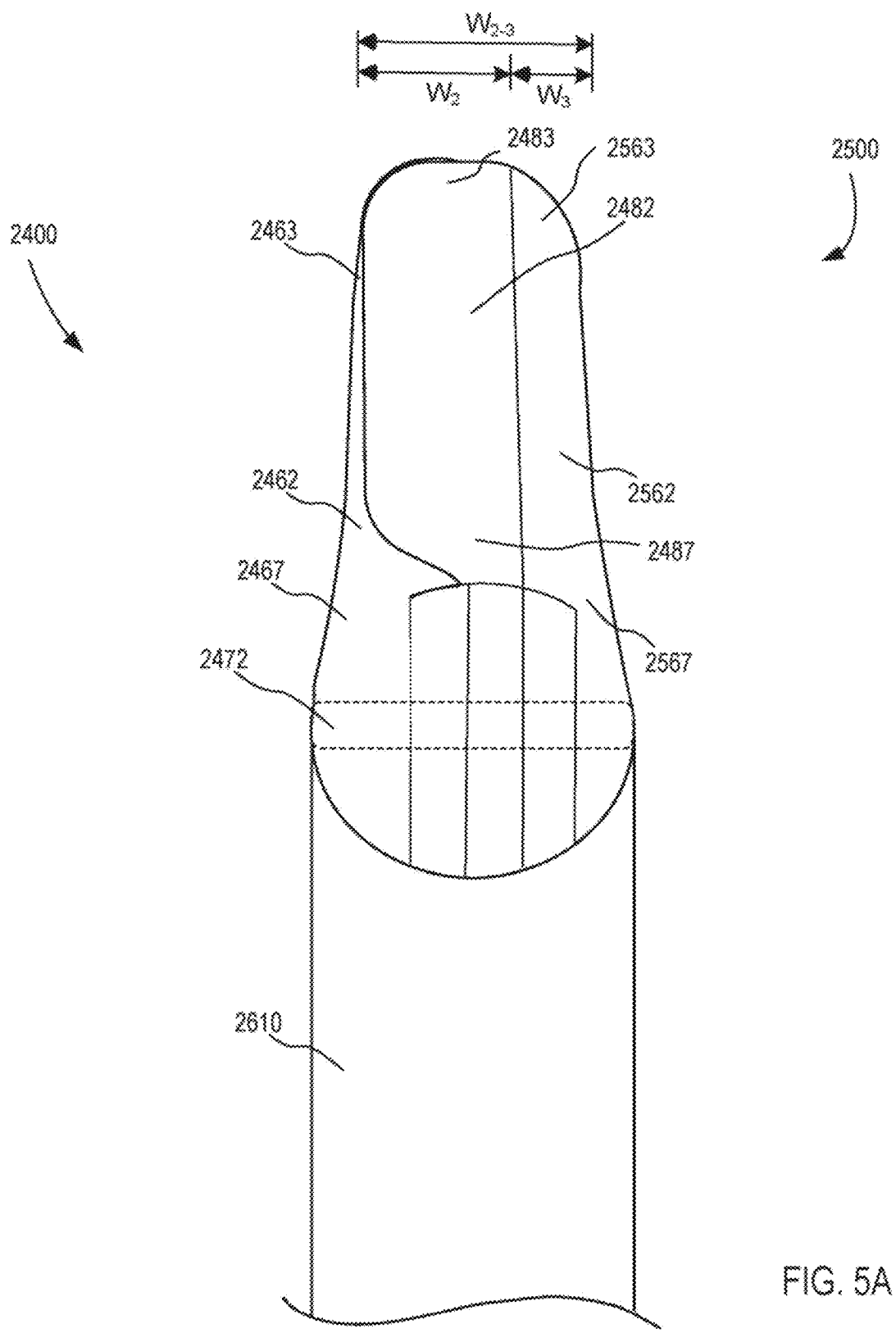
FIG. 5A is a diagrammatic front view of a portion of an instrument of a surgery system shown in a first orientation, according to an embodiment.
Figure 5B:
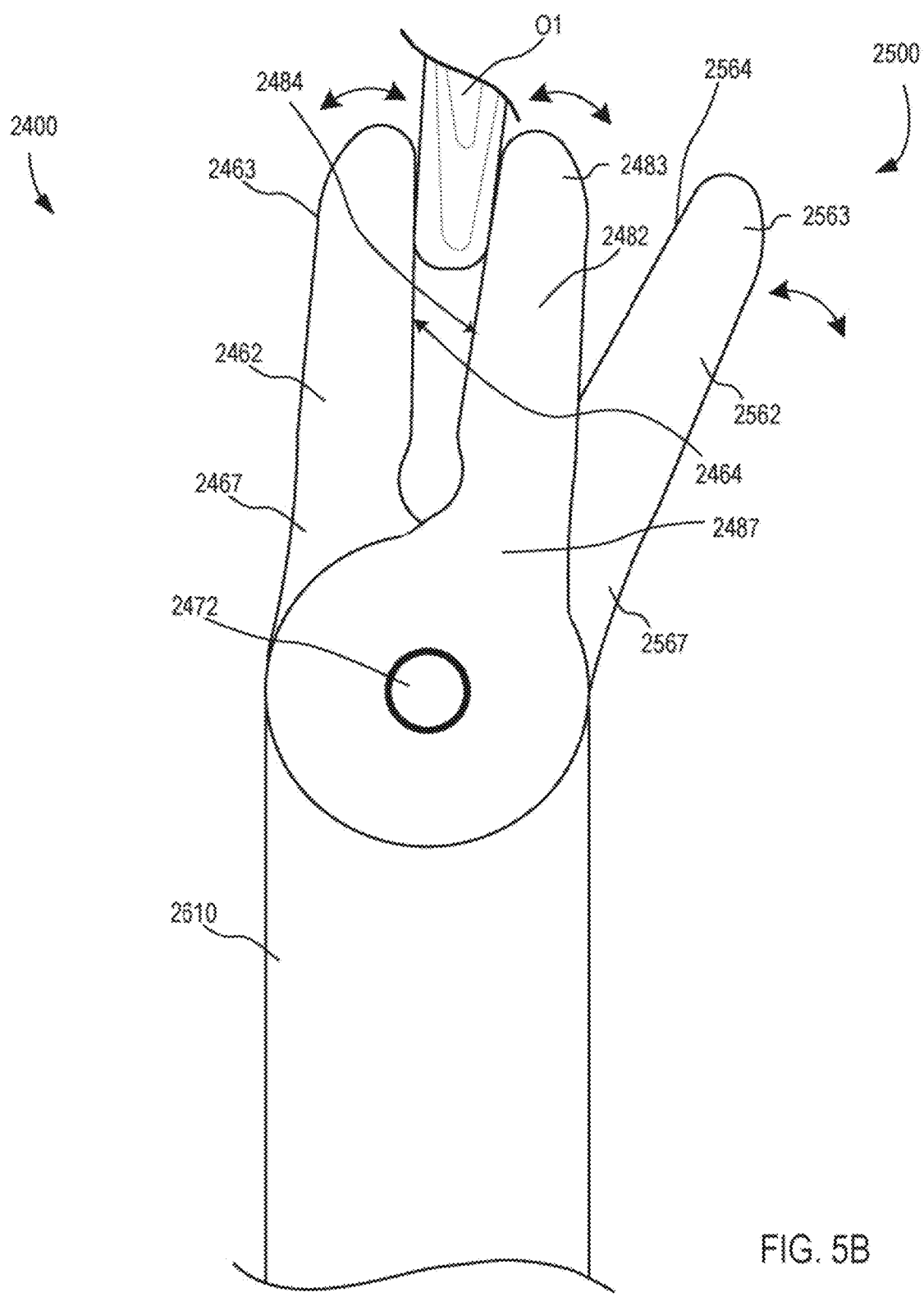
FIG. 5B is a diagrammatic side view of the portion of the instrument of FIG. 5A shown in a second orientation.
Figure 5C:
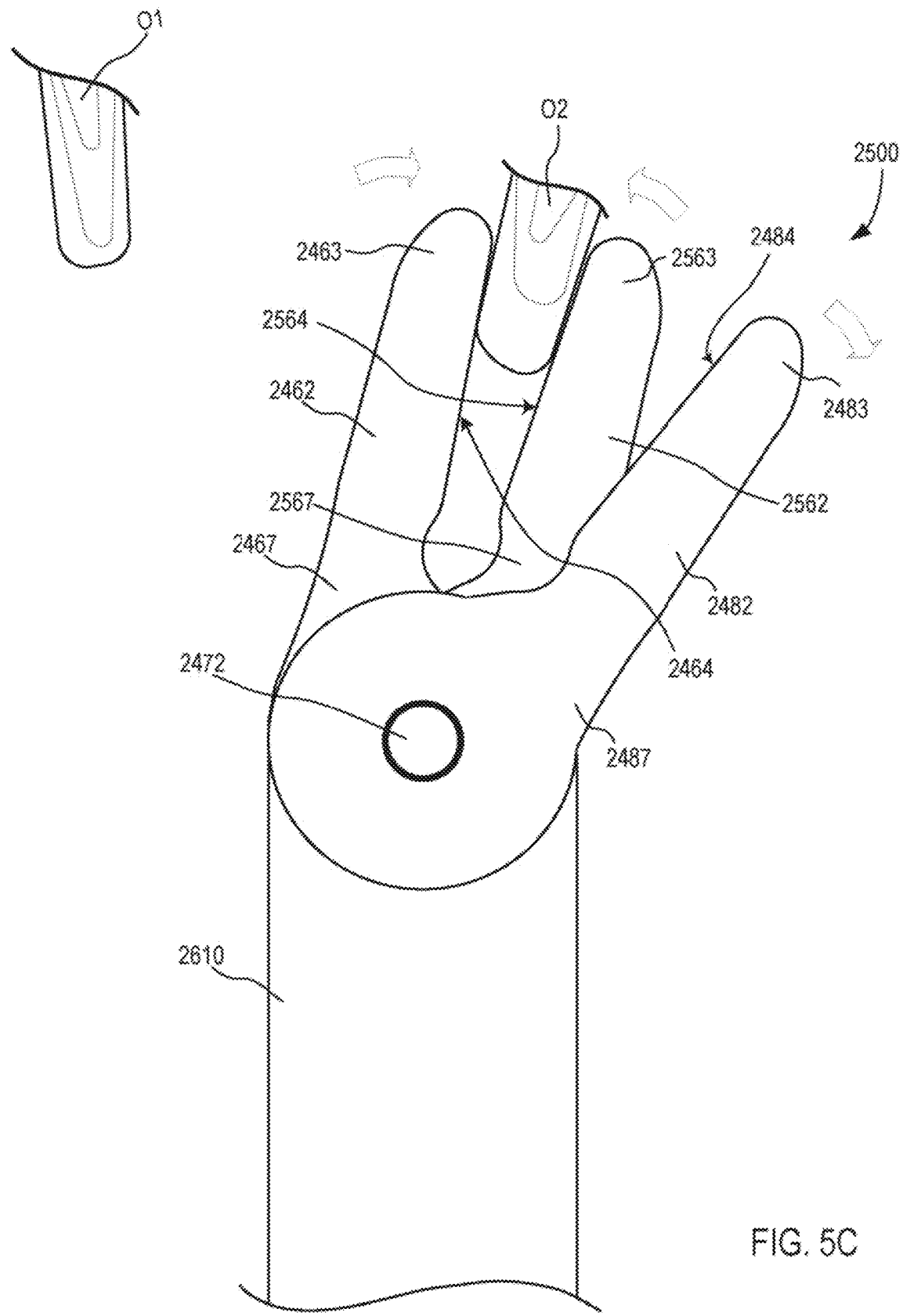
FIG. 5C is a diagrammatic side view of the portion of the instrument of FIG. 5A shown in a third orientation.

It is understood that many different clinical procedures can be performed via instruments 1400 operating through the incision or orifice in the patient P, which can interface with various objects while within the patient including patient tissue, organs, surgical implements like other suture materials or implants, and other cooperating instruments being used for clinical procedures. As such, it can be beneficial for the instruments to be configured as multi-functional instruments for performing multiple clinical functions while within the patient that can minimize the need to switch instruments. Accordingly, FIGS. 5A-5C are diagrammatic illustrations of various portions of a multi-functional instrument 2400 configured as a wrist assembly 2500, according to an embodiment. In some embodiments, the instrument 2400 or any of the components therein are optionally parts of a surgical system that performs minimally invasive surgical procedures and which can include a manipulator unit, a series of kinematic linkages, a series of cannulas, or the like. The instrument 2400 (and any of the instruments described herein) can be used in any suitable surgical system, such as the MIRS system 1000 shown and described above and can be configured to perform multiple clinical functions or interact with multiple objects.

Referring to FIGS. 5A and 5B, the instrument 2400 includes a link 2610, a first tool member 2462, a second tool member 2482, and a third tool member 2562. The link 2610 includes one or more kinematic linkages to an MIRS system 1000 as described above. The first tool member 2462 has a proximal end portion 2467 that is movably coupled to the link 2610 and an opposite distal end portion 2463. Similarly, the second tool member 2482 has a proximal end portion 2487 movably coupled to the link 2610 and an opposite distal end portion 2483. The third tool member 2562 likewise has a proximal end portion 2567 that is movably coupled to the link 2610 and an opposite distal end portion 2563.

The first tool member distal end portion 2463 is configured to engage a first object O1 (FIG. 5B), such as a patient tissue, surgical implement, or other clinical tool as described above. Likewise, the second tool member distal end portion 2483 is configured to engage a second object O2 (FIG. 5C). The third tool member distal end portion 2563 is configured to engage at least one of the first object or the second object. For example, referring to FIG. 5B, the second tool member distal end portion 2483 can be configured to move independently from the third tool member distal end portion 2563, such as to cooperate with the first tool member distal end portion 2463 to engage the first object O1. In this arrangement, the second tool member 2482 is between the first tool member 2462 and the third tool member 2562.

Referring to FIG. 5C, the third tool member distal end portion 2563 can be configured to move independently from the second tool member distal end portion 2483, such as to cooperate with the first tool member distal end portion 2463 to engage the second object O2. In this arrangement, the third tool member 2562 is between the first tool member 2462 and the second tool member 2482. Alternatively, the tool members need not be in a sequential order (i.e., with one tool member being between the others). For example, the first and second tool member distal end portions 2463, 2483 can be configured to grip a first tissue (not shown) therebetween while the third tool member distal end portion 2563 engages a second tissue (not shown). As another example, the third tool member distal end portion 2563 can be configured to move in concert with the second tool member tool member distal end portion 2483 to act as a single tool member to both engage the second object, for example, either with the first tool member 2462 or without the first tool member. For instance, the second and third tool member distal end portions 2483, 2563 can be configured to push against or move a second object, like an organ or patient tissue.

As such, the first tool member 2462 is configured to move relative to the link 2610 independent of movement of the second tool member 2482 and the third tool member 2562. Likewise, the second tool member 2482 is configured to move relative to the link 2610 independent of movement of the first tool member 2462 and the third tool member 2562. Similarly, the third tool member 2562 is configured to move relative to the link 2410 independent of movement of the first tool member 2462 and the second tool member 2482. The first tool member, the second tool member, and the third tool member can each be configured to rotate relative to the link 2610. Further, in some embodiments, the link can be a distal clevis 2610 of the wrist assembly 2500, in which the distal clevis includes a pin 2472 about which at least two of the first tool member, the second tool member, and the third tool member rotate.

Referring to FIGS. 5A-5C, the wrist mechanism 2500 and instrument 2400 can be oriented in any number of different orientations. For example, as shown in FIG. 5A, the instrument 2400 can be in a first (or collapsed) orientation in which the first, second, and third tool members 2462, 2482, and 2562 are oriented in line (or coaxial) with a longitudinal axis (not shown) of the link 2610. This first (or collapsed) orientation is suitable for installation through a cannula or incision (not shown). The instrument 2400 can be moved to other orientations during use while within the patient P, such as the second orientation shown in FIG. 5B and the third orientation shown in FIG. 5C. The beneficial arrangement of three tool members provides a flexible usage, multi-functional instrument 2400 for allowing multiple usage options without needing to switch instruments as often as can occur with conventional instrument designs. For example, in some embodiments the instrument 2400 can be used to grip a first object O1 or tissue between a pair of opposing contact surfaces, such as between a first contact surface 2464 at the distal end portion 2463 of the first tool member 2462, and a second contact surface 2484 at the distal end portion 2483 of the second tool member 2482. The opposing first and second contact surfaces 2464, 2484 can have any number of features as appropriate for engaging object O1 between the opposing gripping surfaces, such as various textures, shapes and gripping features. In such a gripping arrangement formed by opposing contact surfaces, the first contact surface 2464 overlaps the second contact surface 2484 when in the first orientation shown in FIG. 5A.

Referring to FIG. 5A, in some embodiments, the third tool member 2562 can be configured to operate in concert with second tool member 2482 and act as a single tool member when desired. In other words, the second and third tool members 2482 and 2562 can move together as if a single tool member. In such an arrangement, the second tool member 2482 and third tool member 2562 can be oriented in a side-by-side arrangement having the same rotation orientation about pin 2472 with respect to each other. Stated differently, the second and third tool members 2482, 2562 can move together to form a combined, tool member having a larger overall width than each of the individual widths. When in the first orientation shown in FIG. 5A, the second and third tool members 2482, 2562 are aligned with each other such that they have the same rotation orientation about pin 2472. As shown in FIG. 5A, the second tool member 2482 has a width, $W_2$, the third tool member 2462 has a width, $W_3$, and the side-by-side combination of the first and second tool members together have a width, $W_{2-3}$. When controlled to move together as a single side-by-side tool member unit, the second and third tool members can effectively form a single gripping jaw that opposes the first tool member 2462.

Thus, instrument 2400 can be controlled to perform clinical operations that can be performed by a pair of opposing tool members, such as a forceps tool. Additionally, instrument 2400 can be controlled to perform expanded clinical operations as described herein that are able to be performed using all three of the tool members, such as a pair of opposing tool members operating as a gripping or forceps type tool to engage a first target tissue, and the third tool member manipulating a second tissue and/or the third tool member operating as a gripping or forceps type tool with the second tool member to provide a different type of gripping functionality than can be provided by the first and second tool members. As such, instrument 2400 provides an instrument having enhanced operational flexibility for performing multiple clinical functions as desired without needing to switch instruments and/or use multiple instruments simultaneously, which can include combined retractor-type functionality in combination with gripping-type functionality.

The first tool member 2462, the second tool member 2482, and the third tool member 2562 can be moved by any suitable mechanism. For example, in some embodiments, the tool members can be moved by one or more tension members (e.g., cables, bands, or the like). For example, the first tool member 2462 is coupled to a first tension member (not shown), the second tool member 2482 is coupled to a second tension member (not shown), and the third tool member 2562 is coupled to a third tension member (not shown). In this manner, each of the tool members can be moved independently of the other tool members by actuation of the appropriate tension member. In other embodiments, any of the first tool member 2462, the second tool member 2482, and the third tool member 2562 can be moved by a miniature motor, a hydraulic actuator, or the like.

Figure 6A:
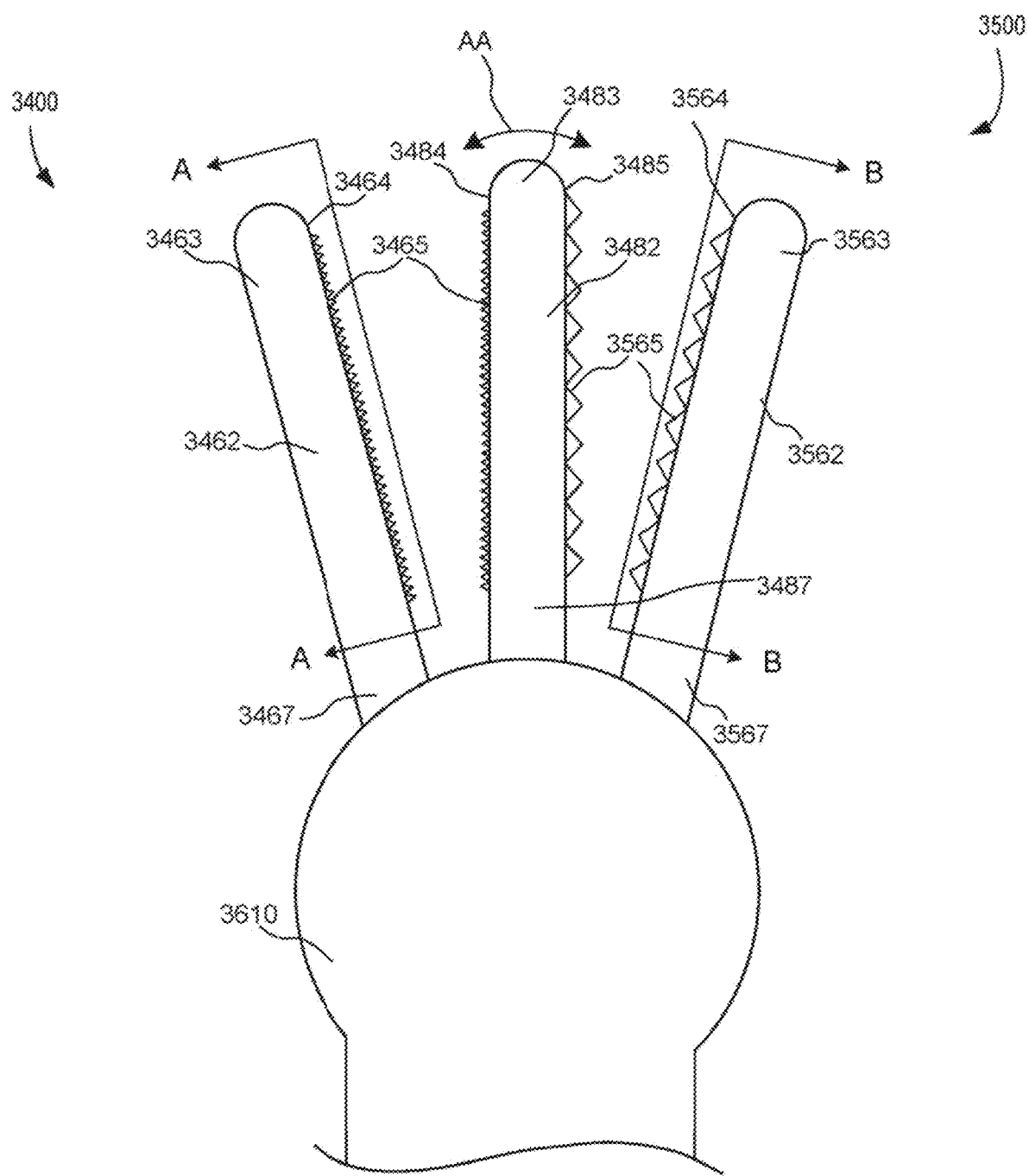
FIG. 6A is a diagrammatic side view of a portion of an instrument of a surgery system shown in a first orientation, according to an embodiment.
Figure 6B:
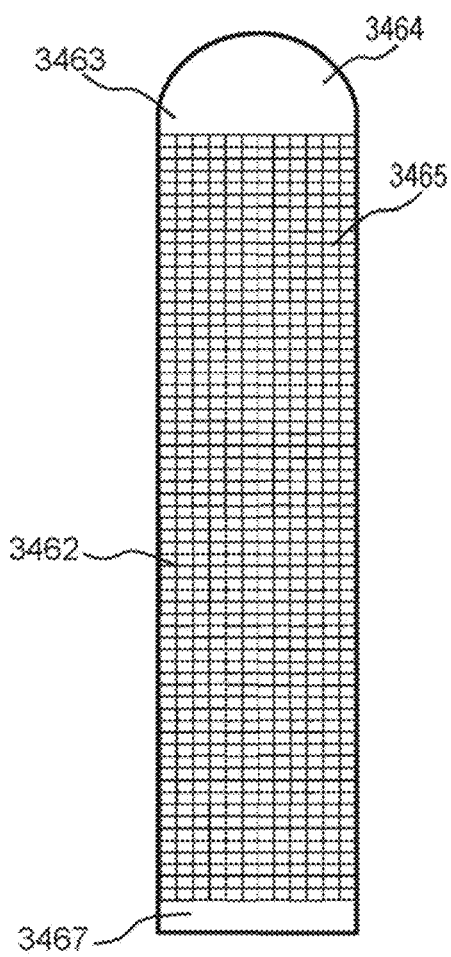
FIG. 6B is a diagrammatic front view of the first contact portion of the first tool member and the first grip pattern of FIG. 6A, as viewed from line A-A shown in FIG. 6A.
Figure 6C:
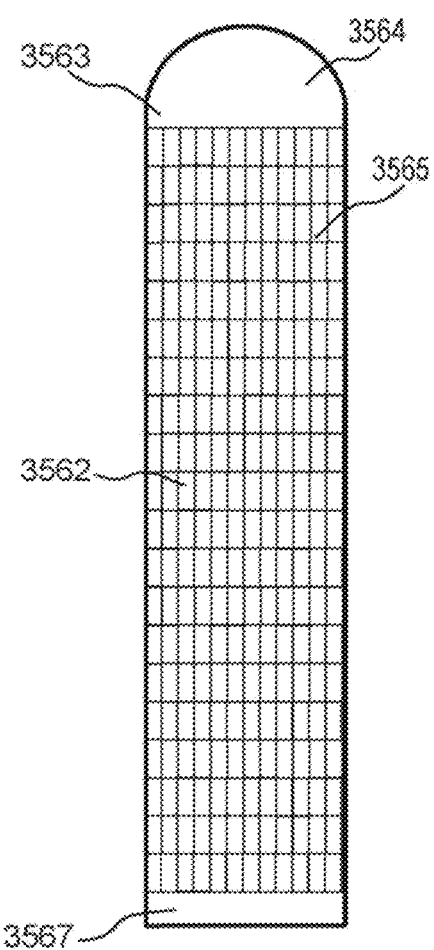
FIG. 6C is a diagrammatic front view of the third contact portion of the third tool member and the second grip pattern of FIG. 6A, as viewed from line B-B shown in FIG. 6A.

In other embodiments, the multiple tool member instruments can be provided in other arrangements, with various features and combinations of features provided by compact arrangements of three tool members coupled to a single instrument. As another example, FIGS. 6A-6C are diagrammatic illustrations of portions of a multi-functional instrument 3400 and wrist assembly 3500 for providing additional combinations and types of clinical functions, according to an embodiment. As with instrument 2400 and wrist assembly 2500, the instrument 3400 or any of the components therein are optionally parts of a surgical system that performs minimally invasive surgical procedures and which can include a manipulator unit, a series of kinematic linkages, a series of cannulas, or the like. Instrument 3400 and wrist assembly 3500 generally includes the same features as described above for instrument 2400 and wrist assembly 2500 except as described herein.

Referring to FIG. 6A, instrument 3400 includes a link 3610, a first tool member 3462, a second tool member 3482, and a third tool member 3562. The first tool member 3462 has a proximal end portion 3467 that is movably coupled to the link 3610 and an opposite distal end portion 3463. The first tool member also has a first contact surface 3464 with a first grip pattern 3565. The second tool member 3482 has a proximal end portion 3487 movably coupled to the link 3610 and an opposite distal end portion 3483. The second tool member 3482 also has a second contact surface 3484 with the first grip pattern 3465 and a fourth contact surface 3485 with a second grip pattern 3565 that is different from the first grip pattern 3465. The first contact surface 3464 and the second contact surface 3484 are configured to manipulate a first object (not shown), such as a first tissue. The third tool member 3562 has a proximal end portion 3567 that is movably coupled to the link 3610 and an opposite distal end portion 3563. The third tool member 3562 also has a third contact surface 3564 with the second grip pattern 3565. The third contact surface 3564 and the fourth contact surface 3485 are configured to manipulate a second object (not shown), such as a second tissue.

In some embodiments, the second contact surface 3484 is on a first side of the second tool member 3482 as shown in FIG. 6A. The second contact surface 3484 is aligned with the first contact surface 3464 when the first contact surface 3464 and the second contact surface 3484 manipulate the first object (not shown), such as a first tissue. The fourth contact surface 3485 is on a second side of the second tool member 3482. The fourth contact surface 3485 is also aligned with the third contact surface 3564, and the second grip pattern 3565 on the third and fourth contact surfaces 3485 and 3564 are aligned with each other when the third contact surface 3564 and the fourth contact surface 3485 manipulate the second object (not shown), such as a second tissue. As such, the second tool member 3482 can be between the first tool member 3462 and the third tool member 3562.

In some embodiments, the second tool member 3484 can rotate relative to the link 3610, as shown by the arrow AA, and the first tool member 3462 and the third tool member 3562 can remain stationary. In other embodiments, each of the first tool member, the second tool member, and the third tool member can each be configured to rotate relative to the link 3610.

The first tool member 3462, the second tool member 3482, and the third tool member 3562 can be moved by any suitable mechanism. For example, in some embodiments, the tool members can be moved by one or more tension members (e.g., cables, bands, or the like). For example, the first tool member 3462 is coupled to a first tension member (not shown), the second tool member 3482 is coupled to a second tension member (not shown), and the third tool member 3562 is coupled to a third tension member (not shown). In this manner, each of the tool members can be moved independently of the other tool members by actuation of the appropriate tension member. In other embodiments, any of the first tool member 3462, the second tool member 3482, and the third tool member 3562 can be moved by a miniature motor, a hydraulic actuator, or the like.

In such an arrangement, the instrument 3400 can be configured to operate as a compact multi-functional instrument that provides multiple forceps-type functions, such as multiple gripping operations. As opposed to instrument 2400, such expanded multi-functional options for instrument 3400 do not include the second and third tool member 3482 and 3562 being configured for a side-by-side arrangement. Rather, the instrument 3400 is configured such that the second tool member 2482 remains between the first tool member 2462 and the third tool member 3562, which can permit different types of multi-functional options in comparison with the instrument 2400. Similar to instrument 2400, each of the tool members 3462, 3482 and 3562 of instrument 3400 can move independently of the other tool members.

Thus, the tool members 3462, 3482 and 3562 can be operated independently to move, to remain stationary and/or to be oriented different from each other, and the tool members can also be operated in various combinations to move together like a single tool member. For example, the first and second tool member 3462 and 3482 can be rotated about the link 3610 to be oriented adjacent to each other such that the first contact surface 3464 of the first tool member interfaces with the second contact surface 3484 of the second tool member to form a first interfaced pair of tool members. The first interfaced pair of tool members can move together and act like a single tool member, such that the second contact surface 3585 on a second side of the second tool member 3482 can move with respect to the third tool member 3562 to function like a dual tool member gripping-type instrument.

Likewise, the second tool member 3482 and the third tool member 3562 can be rotated about the link 3610 to be oriented adjacent to and interfacing with one another such that the second contact surface 3565 of the second tool member 3482 is in contact with the second contact surface 3565 of the third tool member 3562 to form a second interfaced pair of tool members. The second interfaced pair of tool members move together and also act like a single tool member, such that the first contact surface 3465 of the second tool member 3482 can move with respect to the first tool member 3462 to function like dual tool member gripping-type instrument. The second interfaced pair of tool members can provide an additional option for the instrument to function like a dual tool gripping-type instrument. The first interfaced pair of tool members and the second interfaced pair of tool members can each be configured to provide different features and functional options in operation in comparison with the other pair. Thus, the user can have multiple gripping-type functional options and select an appropriate option based on the surgical environment, the patient's needs, clinical functions that each pair can perform, and other factors like the orientation of each of the pairs with respect to a target tissue or other target object for the interfacing pair.

Optionally, the first gripping pattern 3465 defined on the first contact surface 3464 can be configured to matingly interface with the first gripping pattern 3465 defined on the second contact surface 3484 when the first and second tool members act like a single tool member, which can enhance the connection between the first interfaced pair and improve its operability as a gripping-type tool. For example, the first gripping pattern 3465 defined on the second contact surface 3484 can be defined as a mirror image pattern of the first gripping pattern 3465 defined on the first contact surface 3464. The pattern and mirror image pattern of the same of the first and second contact surfaces 3464 and 3484 can more effectively interface with each other to enhance their clinical functionality when operating like a single forceps-type tool.

The arrangements and examples for instrument 3400 described above, the various options for controlling operations of its tool members 3462, 3482 and 3562, as well as other potential options like the interfaced pair options for controlling pairs of the tool members to act as a single gripping-type tool, can provide multi-functional options for the user to take advantage features like the first gripping pattern 3465 in comparison with the second gripping pattern 3565. In addition, the arrangement of instrument 3400 can enable multi-functional options for the user to use instrument 3400 to perform multiple different functions including using both of the gripping patterns 3465 and 3565 to best meet the needs of the surgical environment.

Moreover, the use of multiple gripping patterns 3465 and 3565 with instrument 3400 can provide the user with different functional options for engaging the target tissue with a suitable gripping pattern. Referring now to FIGS. 6B and 6C along with FIG. 6A, the first gripping pattern 3465 and the second gripping pattern 3565 are shown, according to an embodiment. As shown, the first gripping pattern 3465 can be configured for performing a first function, such as providing a fine gripping pattern with high grip strength and tissue engagement purchase for effectively maintaining a grip on the tissue while manipulating the underlying tissue. The second gripping pattern 3565 can be configured for performing a second function, such as configured to have a course gripping pattern 3565 or other specialized pattern directed to impacting tissue within the grip and provide hemostasis functions or other particular functions on the target tissue.

Thus, instrument 3400 can provide a compact, multi-functional instrument for performing different gripping-type clinical functions via a first combination of the tool members operating as a first gripping tool, and expanded clinical functions via a second combination of the tool members operating as a second gripping tool, which additional functionality that can be provided without needing to switch instruments. Further, instrument 3400 can provide optional expanded functionality via the use of three independently-controlled tool members, such as simultaneously interacting with different objects, different tissues or different portions of the same tissue. It is understood, however, that in addition to the gripping-type instruments provided by interactions with tool member combinations of instruments 2400 and 3400, other types of instruments and instrument functionality can be provided based on the controlled actions and interactions of the tool members and combinations of the tool members, such as controlling combinations of the tool members to act as a retractor-type tool, and to do so with or without the instrument also being configured to act as a gripping-type tool.

As another example, FIGS. 7A and 7B show a compact instrument 4400 and wrist assembly 4500 that is configured to perform various clinical functions with respect to target tissue while the instrument is being used within a surgery cavity of a patient, P. However, as described in greater detail below, the instrument 4400 is configured to operate primarily as a retractor-type instrument 4400 as part of a MIS system, rather than operating primarily as a gripping-type instrument, such as instruments 2400 and 3400 that were described in detail above along with the wrist assemblies 2500 and 3500. As such, instrument 4400 may appear to include similar components as described above for instruments 2400 and 3400, but various features, shapes, interconnections and other aspects of the components can differ significantly for such an instrument that was initially configured to provide retractor-type functionality. In addition, movements, actions, and operations related to components of instrument 4400 and wrist assembly 4500 can differ significantly in comparison with the above descriptions for instruments 2400 and 3400.

As used herein, a surgical "retractor" or "retractor-type" clinical instrument refers to a medical instrument having contact surfaces that are configured to engage organs, tissues and/or portions of a surgical cavity or wound to thereby move, hold, lift, retain or otherwise interface with the target tissue and perform clinical retractor-type functions as appropriate for the surgical environment. Thus, as described in detail below, instrument 4400 can be configured to engage target tissue and perform effective retractor functions via controlling its contact with a target tissue. As further described below, instrument 4400 can further be controlled to provide enhanced and additional types of clinical functions along with performing its primary retractor-type functions.

Referring to FIGS. 7A and 7B, instrument 4400 includes a clevis 4610, a pin 4472 coupled to the clevis, a first tool member 4462, a second tool member 4482, and a third tool member 4562. The first tool member 4462 functions as a first blade having a first elongate body including a distal end portion 4463, an opposite proximal end portion 4467, and a first contact surface 4464. The first tool member 4462 is coupled to the clevis 4610 at the proximal end portion 4467 of the first tool member for rotation with respect to the clevis about the pin 4472. The second tool member 4482 functions as a second blade having a second elongate body including a distal end portion 4483, an opposite proximal end portion 4487, a second contact surface 4484 on one side of the second blade, and a fourth contact surface 4485 on the other side of the second blade. The second tool member 4482 is coupled to the clevis 4610 at the proximal end portion of the second tool member for rotation with respect to the clevis 4610 about the pin 4472. The third tool member 4562 functions as a third blade having a third elongate body including a distal end portion 4563, an opposite proximal end portion 4567, and a third contact surface 4564. The third tool member 4562 is coupled to the clevis 4610 at the proximal end portion of the third tool member for rotation with respect to the clevis 4610 about the pin 4472.

As shown in FIG. 7A, each of the first, second and third tool members 4462, 4482, and 4562 are aligned with each other and with a centerline CL of the instrument 4400 when in a first orientation, which provides a compact orientation for installation and removal of the instrument through a cannula with respect to a surgical environment (not shown). While in the compact first orientation of FIG. 7A, the centerline CL of the instrument 4400 is oriented to be coaxial with a longitudinal axis (not shown) of an instrument shaft that controllably connects the instrument 4400 to a transmission assembly of a MIS surgical system as described above. After installation of the instrument 4400 into the surgical environment (not shown), the instrument 4400 can independently rotate the tool members 4462, 4482 and 4562 with respect to the clevis 4610 according to the surgical environment to place the instrument 4400 to an extended second orientation (see e.g., FIG. 7B) that can have any number of orientations for the tool members.

Referring to FIG. 7B, the first contact surface 4464 is defined on a first side of the first tool member 4462. The first contact surface 4464 is oriented toward and faces the second tool member 4482 that is adjacent to it when in the first orientation shown in FIG. 7A. Similarly, the second contact surface 4484 is defined on a first side of the second tool member 4482. The second contact surface 4484 and the first contact surface 4464 have an opposing relationship such that first and second contact surfaces are oriented toward and face each other when in the first orientation shown in FIG. 7A. The fourth contact surface 4485 of the instrument 4400 is defined on a second side of the second tool member 4482 that is opposite its first side. The third contact surface 4564 is defined on a first side the third tool member 4562. The third contact surface 4564 and the fourth contact surface 4485 have an opposing relationship such that third and fourth contact surfaces are oriented toward and face each other when in the first orientation shown in FIG. 7A.

As is further shown in FIGS. 7A and 7B, instrument 4400 can include a first tension member 4420, a second tension member 4430, and a third tension member 4440. Each of the tension members 4410, 4430 and 4440 can be attached to a transmission assembly (not shown) of an MIS system that can function as an actuator mechanism to move each of the tension members independently and, thereby, independently control movement of each one of the tool members. A proximal end portion 4467 of the first tool member 4462 can be coupled to the first tension member 4420, such that the first tool member is rotatable relative to the clevis 4610 when the first tension member is moved that rotates a distal end portion 4463 of the first tool member. Similarly, a proximal end portion 4487 of the second tool member 4482 is coupled to the second tension member 4430, such that the second tool member is rotatable relative to the clevis 4610 when the second tension member is moved that rotates a distal end portion 4483 of the second tool member. Additionally, a proximal end portion 4567 of the third tool member 4562 is coupled to the third tension member 4440, such that the third tool member is rotatable relative to the clevis 4610 when the third tension member is moved that rotates a distal end portion 4563 of the third tool member.

Each of the first, second and third tool members 4462, 4482 and 4562 can have the same rotational axis for rotations with respect the clevis 4610 about pin 4472. Further, each of the first, second, third and fourth contact surfaces of the tool members are oriented to be parallel with each other throughout the range of rotations for each tool member with respect to the clevis, and to be maintained parallel with the other contact surfaces regardless of the tool member rotations and orientations. When one or more of the first, second and third blades 4462, 4482 and 4562 are rotated to be fully or partially aligned another blade, the corresponding parallel contact surfaces of the aligned or partially aligned blades can cooperate with each other to form a fan-shaped wall of parallel contact surfaces that can be beneficial for manipulating or moving organs or tissues requiring a continuous or semi-continuous interface. In addition, two or more of the first, second and third blades can be aligned with each other to reinforce and enhance the flex strength of the blades.

As described in detail above, instruments 2400 and 3400 can each provide compact, multi-functional instruments for performing gripping-type clinical functions via a first combination of the tool members operating as a first gripping tool, and expanded clinical functions via a second combination of the tool members operating as a second gripping tool, in which each instrument includes three tool members that cooperate to provide additional functionality that can be provided without needing to switch instruments. Further, as described above, instrument 4400 can provide a highly controllable, compact instrument having three tool members that can cooperate to perform various retractor-type clinical functions in a wide variety of customizable sizes and arrangements, which can be configured repeatedly while in a surgical environment without needing to switch instruments. It is understood that, in other embodiments, various types and combinations instrument functionality can be provided for instruments having three independently controllable tool members, such as the same instrument being configured to provide one or more gripping-type functions and to provide retractor-type functions without switching instruments. As an example, FIGS. 8A-18 show various views of an instrument 5400, according to an embodiment, having three independently controllable tool members that is configured to perform both gripping-type functions and retractor-type functions without switching instruments. The instrument 5400 (and any of the instruments described herein) can be used in any suitable surgical system, such as the MIRS system 1000 shown and described above.

Referring to FIGS. 8A-13, the instrument 5400 includes a transmission assembly 5700 (that can function as an actuator mechanism or transmission mechanism), an instrument shaft 5410, a wrist assembly 5500, and an end effector 5460. As with instruments 2400, 3400 and 4400, instrument 5400 includes one or more tension members that have largely been omitted in FIGS. 9-16B to show more clearly various features pertaining to the three controllable, rotatable tool members of the end effector 5460, as well as pertaining to controlling operations of the three tool members to perform various combinations of clinical functions without switching instruments. However, for clarity purposes, a portion of each corresponding tension member for the respective tool members discussed hereafter is shown in FIGS. 9-13 to illustrate related features discussed herein, such as operability of one or more of the tool members for various clinical and medical functions and independent control of each of the tool members. Further, the illustrated portions of the tension members show respective routing of the tension members through the instrument 5400 along with coupling of each tension member with the respective tool member.

Although referred to herein as tension members or cables, it is understood that various other types of drive components, members, or mechanisms, and/or actuation components, members, or mechanisms can be arranged to implement force-transmitting and orientation-controlling actions with respect to components of instrument 5400 including with respect to its tool members. These features can further cooperate with one or more additional drive mechanisms to implement these actions with respect to the instrument 5400, such as having force applied to components of the instrument via the transmission 5700, or such components being actuated or driven via the transmission 5700, in order to implement desired effects for each of the tool members and perform various clinical and medical functions.

Referring to FIGS. 8A-8C, the instrument 5400 includes a first tension member 5420 (which functions as an actuation member, a second tension member 5430 (which functions as an actuation member), a third tension member 5440 (which functions as an actuation member), and a fourth tension member 5450 (which functions as an actuation member) that couple the transmission 5700 to the wrist assembly 5500. The instrument 5400 is configured such that movement of the tension members can produce rotation of the wrist assembly 5500 (i.e., pitch rotation), yaw rotation of the end effector 5460, grip rotation of the tool members of the end effector 5460 about the yaw axis, or any combination of these movements in the performance of clinical and medical functions. Changing the pitch, yaw, or grip of the instrument 5400 can be performed by manipulating the four tension members.

The transmission 5700 produces movement of each of the first tension member 5420 and the second tension member to produce the desired movement (pitch, yaw, or grip) at the wrist assembly 5500. Specifically, the transmission 5700 includes components and controls to move some of the tension members in a proximal direction (i.e., to pull in certain tension members) while simultaneously allowing the distal movement (i.e., releasing or "paying out") of other of the tension members. In this manner, the transmission 5700 can maintain the desired tension within the tension members, and, in some embodiments, can ensure that the lengths of the tension members are conserved (i.e., moved in equal amounts) during the entire range of motion of the wrist assembly 5500.

The transmission 5700 includes a chassis 5760, a first capstan assembly 5710, a second capstan assembly 5720, a third capstan assembly 5730, a fourth capstan assembly 5740, a roll actuator 5750, and a tension member guide 5800. The chassis 5760 (which functions as a housing) provides the structural support for mounting and aligning the components of the transmission 5700. For example, as shown in FIG. 8A, the chassis 5760 defines a first opening within which the proximal end portion 5411 of the shaft 5410 is mounted, and multiple second openings within which the capstan assemblies are mounted. The chassis 5760 includes an upper housing 5765 that provides additional mounting surfaces and support (e.g., for the capstan assemblies).

The shaft 5410 can be any suitable elongated shaft that couples the wrist assembly 5500 and the end effector 5460 to the transmission 5700. Specifically, the shaft 5410 includes a proximal end portion 5411 that is coupled to the chassis 5760. The shaft 5410 defines at least one passageway through which the first tension member 5420, the second tension member 5430, the third tension member 5440, the fourth tension member 5450, and other components (e.g., energized electrical wires, ground wires, or the like, not shown) can be routed from the transmission 5700 towards the wrist assembly 5500. Moreover, although the chassis 5760 is shown as defining an opening within which the proximal end portion of an instrument shaft 5410 is mounted, in other embodiments, the shaft 5410 can be coupled to the chassis 5760 by any suitable mechanism (e.g., a flange connection).

In addition to providing mounting support for the internal components of the transmission 5700, the chassis 5760 can also include external features (not shown, but which can be recesses, clips, etc.) that interface with a docking port of a drive device (not shown). The drive device can be, for example, a computer-assisted teleoperated surgical system that can receive the transmission 5700 and manipulate the transmission 5700 to perform various surgical operations. In other embodiments, the drive device can be an assembly system that can receive and manipulate the transmission 5700 to perform various assembly operations.

The first capstan assembly 5710 includes a shaft that can be motor-driven to rotate about a capstan axle. The rotating shaft includes a portion about which an end portion of the first tension member 5420 is wrapped. Thus, when the first capstan assembly 5710 rotates in a first direction, the first tension member 5420 can be moved proximally (i.e., can be pulled inward or wrapped about the rotating shaft), and when the first capstan assembly 5710 rotates in a second direction, the first tension member 5420 can be moved distally (i.e., can be payed-out or unwrapped from the rotating shaft). In a similar manner, the second capstan assembly 5720 includes a shaft about which an end portion of the second tension member 5430 is wrapped, the third capstan assembly 5730 includes a shaft about which an end portion of the third tension member 5440 is wrapped, and the fourth capstan assembly 5740 includes a shaft about which an end portion of the fourth tension member 5450 is wrapped, and so on according to the number and arrangements of tension members appropriate for implementing desired medical and clinical functions. Referring to FIG. 8B, the arrangement of the capstan assemblies and the tension member guide 5800 defines a tension member path for each of the tension members. Through these tension member paths, the tension members are routed from their respective capstan assembly into the shaft 5410.

The roll actuator 5750 includes a shaft that can be motor-driven to rotate about an axle. The rotating shaft includes a gear that meshes with a shaft gear 5755 (see FIG. 17) coupled to the shaft 5410. Thus, when the roll actuator 5750 rotates in a first direction, the shaft gear 5755 (and thus the shaft 5410) can be rotated in a first direction, and when the roll actuator 5750 rotates in a second direction, the shaft gear 5755 can be rotated in a second direction. The rotation of the shaft about the shaft axis (which functions as a roll axis; the term roll is arbitrary) is shown by the arrow DD in FIGS. 8B and 17.

Figure 9:
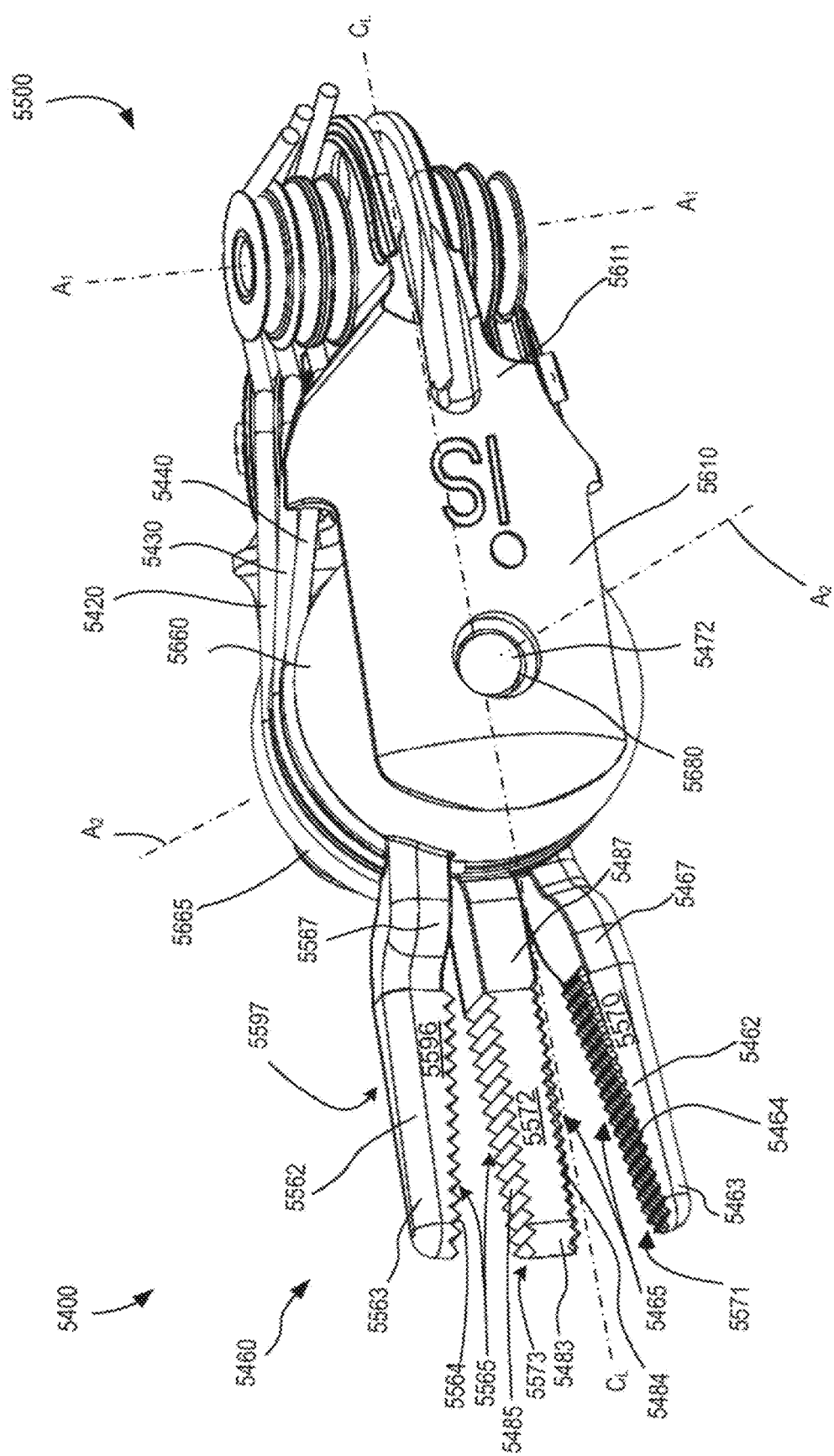
FIG. 9 is an enlarged perspective view of a distal end portion of the instrument in the first orientation indicated by the region Z shown in FIG. 8A, according to an embodiment.

Referring to FIG. 9, instrument 5400 includes a first tension member 5420 that is coupled to the first proximal end portion 5467 of the first tool member 5462. In addition, the instrument 5400 includes a second tension member 5430 that is coupled to the second proximal end portion 5487 of the second tool member 5482. Further, the instrument 5400 includes a third tension member 5440 that is coupled to a third proximal end portion 5567 of the third tool member. Further, the instrument 5400 generally includes multiple tension members that couple the transmission mechanism 5700 to the wrist assembly 5500. The instrument 5400 is configured such that movement of the tension members can produce rotation of the wrist assembly 5500 (i.e., pitch rotation) about a first axis of rotation, $A_1$, yaw rotation of the end effector 5460 about a second axis of rotation, grip rotation of the tool members of the end effector 5460 about the yaw axis, $A_2$, or any combination of these movements. Thus, the instrument 5400 is configured to perform a variety of articulation movements along portions of the wrist assembly 5500 and the end effector 5460.

The transmission mechanism 5700 produces movement of the plurality of tension members (that also function as actuation members) as described above along with FIGS. 8A-8C, which operate to produce the desired articulation movements (pitch, yaw, or grip) at the wrist assembly 5500. Specifically, the transmission mechanism 5700 includes components and controls to move some of the tension members in a proximal direction (i.e., to pull in certain tension members) while simultaneously allowing the distal movement (i.e., releasing or "paying out") of other of the tension members in equal lengths. In this manner, the transmission mechanism 5700 can maintain the desired tension within the tension members, and can ensure that the lengths of the tension members are conserved (i.e., moved in equal amounts) during the entire range of motion of the wrist assembly 5500. In some embodiments, for example, the transmission assembly 5700 can be any of the transmission assemblies shown and described in International Patent Application No. PCT/US2017/062258, (filed Nov. 14, 2017), entitled "Cable Length Conserving Medical Instrument," which is incorporated herein by reference in its entirety. In other embodiments however, conservation of the lengths of the tension members is not required.

Referring now to FIG. 8A, the wrist mechanism 5500 of the instrument 5400 is coupled to the shaft 5410, which can be any suitable elongated shaft that couples the wrist assembly 5500 to the transmission mechanism 5700. Specifically, the instrument shaft 5410 includes a proximal end portion 5411 that is coupled to a housing of the transmission mechanism 5700, and a distal end portion 5412 that is coupled to the wrist assembly 5500. The instrument shaft 5410 defines a passageway or series of passageways through which the tension members (that also function as actuation members), non-drive wires and other components (e.g., electrical wires, ground wires, or the like) can be routed from the transmission mechanism 5700 to the wrist assembly 5500. Although shown as being cylindrical, in other embodiments the instrument shaft 5410 can have any suitable shape.

Referring now to FIGS. 9-13, the wrist assembly 5500 of the instrument 5400 includes the end effector 5460 and a distal clevis 5610. A proximal end 5611 of the distal clevis 5610 is articulably coupled to the instrument shaft, either directly or via a proximal clevis 5510 (that also functions as a link). A pin 5640 couples the proximal clevis 5610 to the proximal end 5611 of the distal clevis 5610. The distal clevis 5610 can rotate relative to the proximal clevis 5510 that is connected to the instrument shaft about pin 5640. In this manner, the distal clevis 5610 can be articulably coupled to the instrument shaft. A distal end 5612 of the distal clevis 5610 further includes a connector 5680 that is coupled to the end effector 5460. In this manner, a first tool member 5462, a second tool member 5482, and a third tool member 5562 of the end effector 5482 can rotate relative to the clevis 5610 about a second axis of rotation, $A_2$. (also referred to as the yaw axis). The connector 5680 is a pin-type connector and includes a pin supported by (and placed within) the pin openings. In some embodiments, the connector 5680 can include any of the structure and features of the pinned joints shown and described in U.S. Pat. No. 9,204,923 B2 (filed Jul. 16, 2008), entitled "Medical Instrument Electronically Energized Using Drive Cables," which is incorporated herein by reference in its entirety. As shown in FIG. 8A, the second axis of rotation (also referred to as the yaw axis) is non-parallel to the pitch axis $A_1$. Thus, the instrument 5400 provides for up to three degrees of freedom (i.e., a pitch motion about the first axis of rotation $A_1$, a yaw rotation about a second axis of rotation, and a grip motion about the second axis of rotation).

Referring now to FIG. 9, each of the tool members are coupled to the distal clevis at a proximal end portion, and include one or more grip surfaces as well as contact surfaces on their side portions. As is described in greater detail below, the one or more grip surfaces provide options for the instrument 5400 to perform various grip-type functions, and the contact surfaces provide options for the instrument to also perform various retractor-type functions. In particular, the first tool member 5462 has a proximal end portion 5467 that is movably coupled to the distal clevis 5610, and an opposite distal end portion 5463. Further, the first tool member has a first grip surface 5464 having a first grip pattern 5565, and also has a first contact surface 5570 disposed on a first side portion, and a second contact surface 5571 disposed on an opposite second side portion. Similarly, the second tool member 5482 has a proximal end portion 5487 movably coupled to the distal clevis 5610, and an opposite distal end portion 5483. Further, the second tool member has a second grip surface 5484 having the first grip pattern 5565, and also has a first contact surface 5572 disposed on a first side portion, and a second contact surface 5573 disposed on an opposite second side portion. In addition, the second tool member 5482 also has a fourth grip surface 5485 having a second grip pattern 5565 that is different from the first grip pattern 5465. The third tool member 5562 has a proximal end portion 5567 that is movably coupled to the distal clevis 5610, and an opposite distal end portion 5563. The third tool member 5562 also has a third grip surface 5464 having the second grip pattern 5565, as well as a first contact surface 5596 disposed on a first side portion, and a second contact surface 5597 disposed on an opposite second side portion.

Cooperating pairs of the first, second, third and fourth grip surfaces 5464, 5484, 5485 and 5564 are configured to work together to perform clinical grip functions. For example, the first and second grip surfaces 5464, 5484 of the first and second tool members 5462, 5482 are configured to cooperate to perform first grip functions. As such, the second grip surface 5484 on the second tool member 5482 is located on a first side of the second tool member 5482 and is directed toward the first grip surface 5464 on the first tool member. Moreover, the first grip surface 5464 and the second grip surface 5484 are aligned with each other when the first tool member 5462 and the second tool member 5482 are controller together to perform the first grip functions, which can be performed based on the surgical environment. For example, the first and second grip surfaces 5464, 5484 include the first gripping pattern 5465, which can be configured for interacting with particular types of tissues or doing so in a particular manner, such as for providing a high grip strength to be applied to solid tissues like bone material. The first grip pair can also be configured to perform the first grip functions based on various other parameters, such as location and orientation of first and second tool members, grip strength characteristics configured for the pair, and the shape and design of the corresponding jaws. Further, the first grip pair can be configured to perform the first grip functions according to a sequence or timing, such as performing the first grip functions to manipulate a first object (not shown), such as a first tissue at a first time.

In addition, the third and fourth grip surfaces 5564, 5565 of the third and second tool members 5562, 5482 are configured to cooperate to perform second grip functions. As such, the fourth grip surface 5485 on the second tool member 5482 is located on a second side of the second tool member, and is directed toward the third grip surface 5564 on the third tool member. Moreover, the third grip surface 5564 and the fourth grip surface 55485 are aligned with each other when the second tool member 5482 and the third tool member 5562 are controller together to perform the second grip functions, which can also be performed according to the surgical environment. For example, the third and fourth grip surfaces 5564, 5485 include the second gripping pattern 5565, which can also be configured for interacting with particular types of tissues or doing so in a particular manner, such as for manipulating tissue to slow or stop bleeding for soft tissues. The second grip pair can also be configured to perform the second grip functions based on various other parameters, such as the location and orientation of second and third tool members, levels of control for sensitive applications of force, and the shape and design of the corresponding jaws. Further, the second grip pair can be configured to perform the second grip functions according to a sequence or timing, such as performing the second grip functions to manipulate a second object (not shown), such as to slow or stop bleeding in the first tissue at a first time prior to the first grip functions, or to apply tension on a second tissue to assist with its removal.

Figure 10:
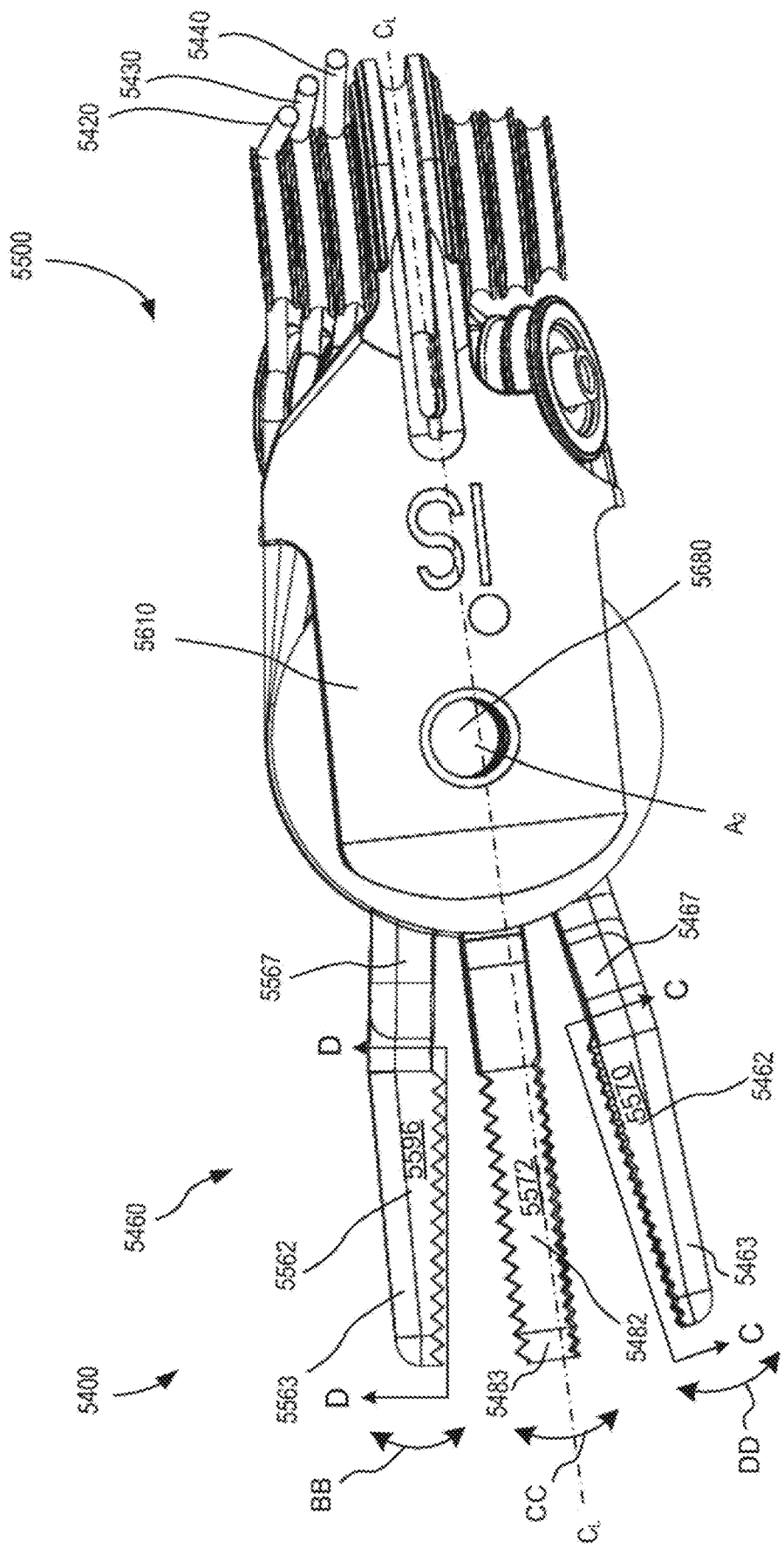
FIG. 10 is an enlarged side view of the distal end portion of the instrument in the first orientation indicated by the region Z shown in FIG. 8A, according to an embodiment.

Referring to FIGS. 10 and 14A-16B, the first and second grip patterns 5465, 5565 according to the views C-C and D-D identified in FIG. 10 are shown in greater detail for the first and second grip pairs discussed above. Referring to FIGS. 14A, 14B and 16A, the first gripping surface 5464 of the first tool member 5462 is shown along with the second gripping surface 5484 of the second tool member. Although all grip surfaces can include the same gripping patterns, the instrument 5400 has been configured to provide different gripping patterns, which can enhance the range and quality of clinical functions that can be performed by instrument 5400.

By way of example, the first gripping pattern has been configured to include multiple series of tooth-like engagement features across the first and second gripping surfaces 5464 and 5484, which can enhance gripping and retention forces during use with respect to a target tissue. The first gripping pattern 5465 can be a general gripping pattern that can enhance gripping functionality in many circumstances and for gripping a wide variety of tissues, which can be used alone or optionally in combination gripping functions that are performed along use of the second gripping pattern 5565.

Figure 15B:
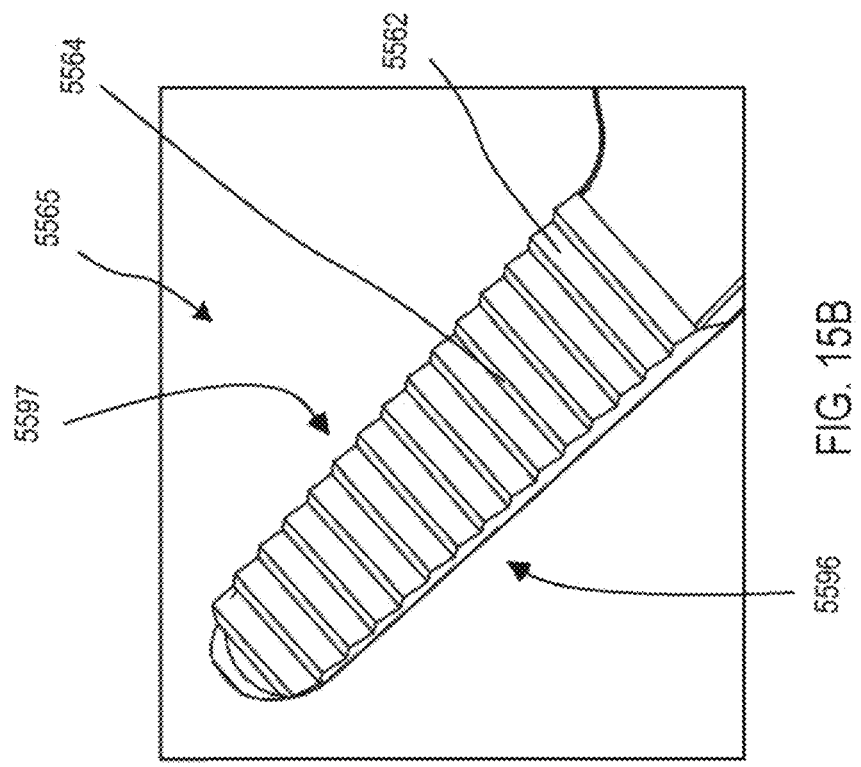
FIG. 15B is a perspective view of the fourth gripping portion of the second tool member and the second grip pattern of the instrument of FIG. 8A.
Figure 15A:
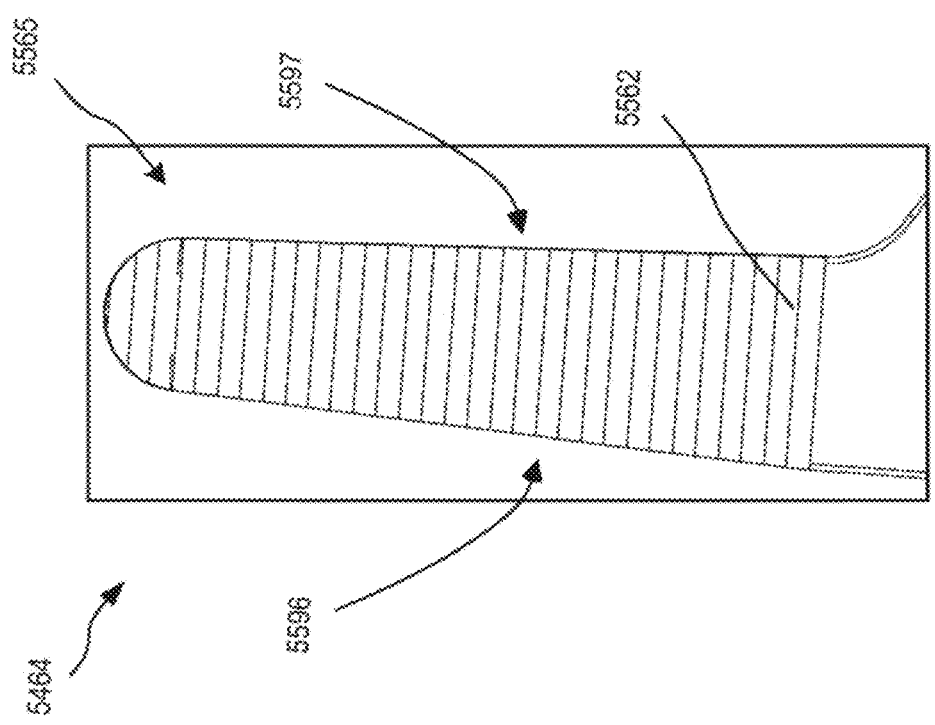
FIG. 15A is a perspective view of the second gripping portion of the second tool member and the first grip pattern of the instrument of FIG. 8A, viewed from line D-D shown in FIG. 10.
Figure 16B:
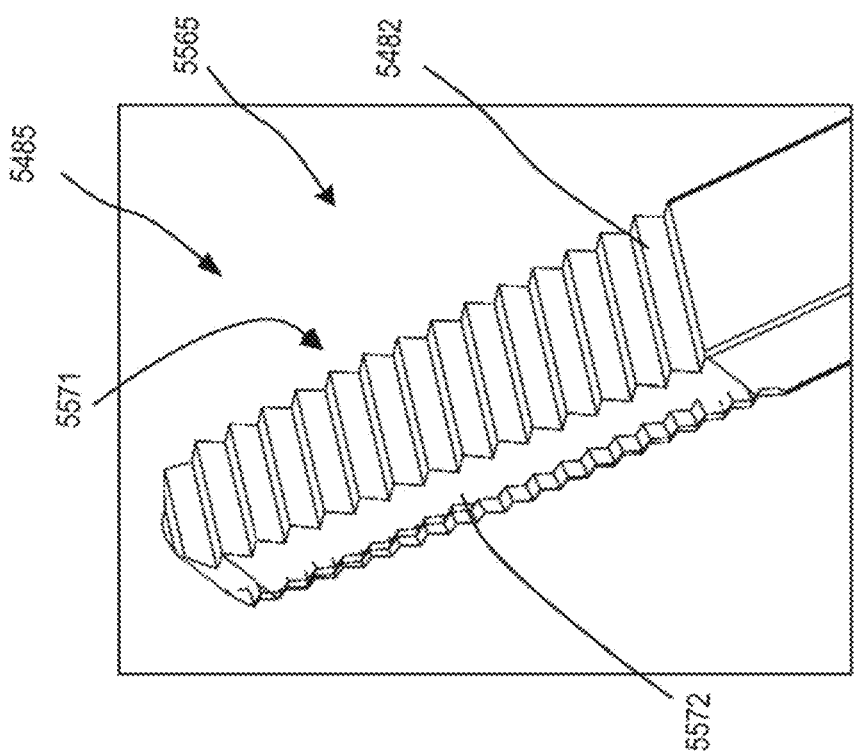
FIG. 16B is a perspective view of the fourth gripping portion of the second tool member and the second grip pattern of the instrument of FIG. 8A.
Figure 16A:
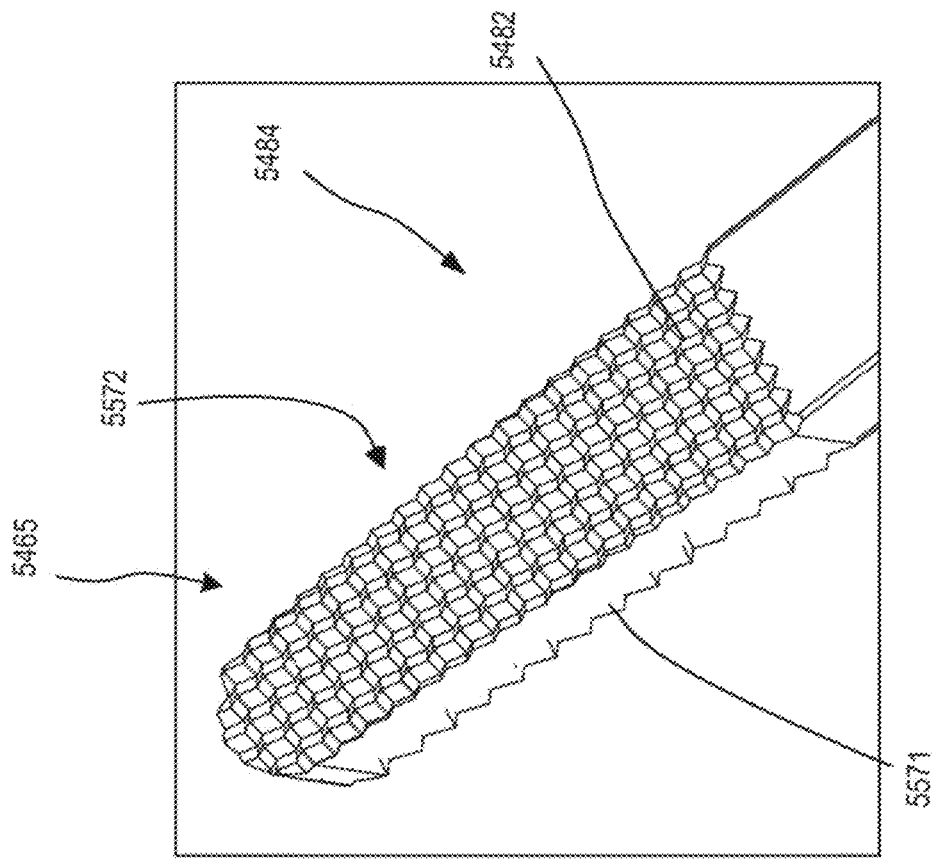
FIG. 16A is a perspective view of the second gripping portion of the second tool member and the first grip pattern of the instrument of FIG. 8A.

Referring to FIGS. 15A, 15B and 16B, the second gripping pattern 5565 of the third grip surface 5564 and the fourth grip surface 5585 is generally shown. Rather than including multiple series of small projections similar to those that form a general gripping pattern can be uses for the first gripping pattern 5465, as an example, the second gripping pattern 5565 can include a customized gripping pattern 5565. Combinations of different gripping patterns for the grip surface of instrument 5400 can provide enhanced functionality and usage options for the instrument. In addition, combinations of different grip patterns can provide further benefits including providing instrument 5400 with a generally applicable gripping pattern and a customized gripping pattern that can be highly beneficial in certain circumstances that occur less frequently.

Second gripping pattern 5565 shows, by way of example, a customized gripping pattern that can be highly beneficial in certain circumstances, such as for stopping or slow blood loss in a target tissue and/or to provide enhance directional grip, such as for pulling or applying a tensile force to a target tissue. As such, the second gripping pattern 5565 includes an alternating series of angled projections and grooves that can be used to concentrate forces applied to tissue via clamping in a pattern that can help slow or stop bleeding. Further, the second gripping pattern 5565 includes rows extending in the widthwise direction with respect to the gripping surfaces, which can provide enhanced retention of gripped tissue in an orientation that is perpendicular with respect to directional rows of the grip pattern.

Further, it is understood that many different types of gripping patterns in many different combinations can be incorporated into instrument 5400. Options for incorporating different gripping patterns, on its own, can increase the overall versatility and effectiveness of instrument 5400. Configuring instrument 5400 to include combinations of gripping patterns according to anticipated usage and/or a surgical environment can be highly beneficial, such as instrument 5400 readily performing gripping functions with beneficial gripping patterns without needing to switch gripping tools or instruments.

Referring to FIGS. 9-13, various aspects and features described above for embodiments 2400, 3400 and 4400 have been incorporated into instrument 5400, which if pursued can significantly expand its multi-functional capabilities even further. As described above along with FIG. 9 while describing features of the first, second and third tool members, each of the tool members include a first and a second contact portion at their side portions that are oriented parallel with each other, and that are configured to remain parallel with each other throughout the independent rotations of the tool members (see e.g., FIG. 13) regarding the parallel orientations of the contact portions at the side portions). In particular, the first tool member 5462 includes first contact portion 5470 at a first side portion and second contract portion 5471 at an opposite second side portion. Likewise, the second tool member 5482 includes first and second contact portions 5572 and 5573. Further, the third tool member 5562 includes first and second contact portions 5596 and 5597.

Figure 11:
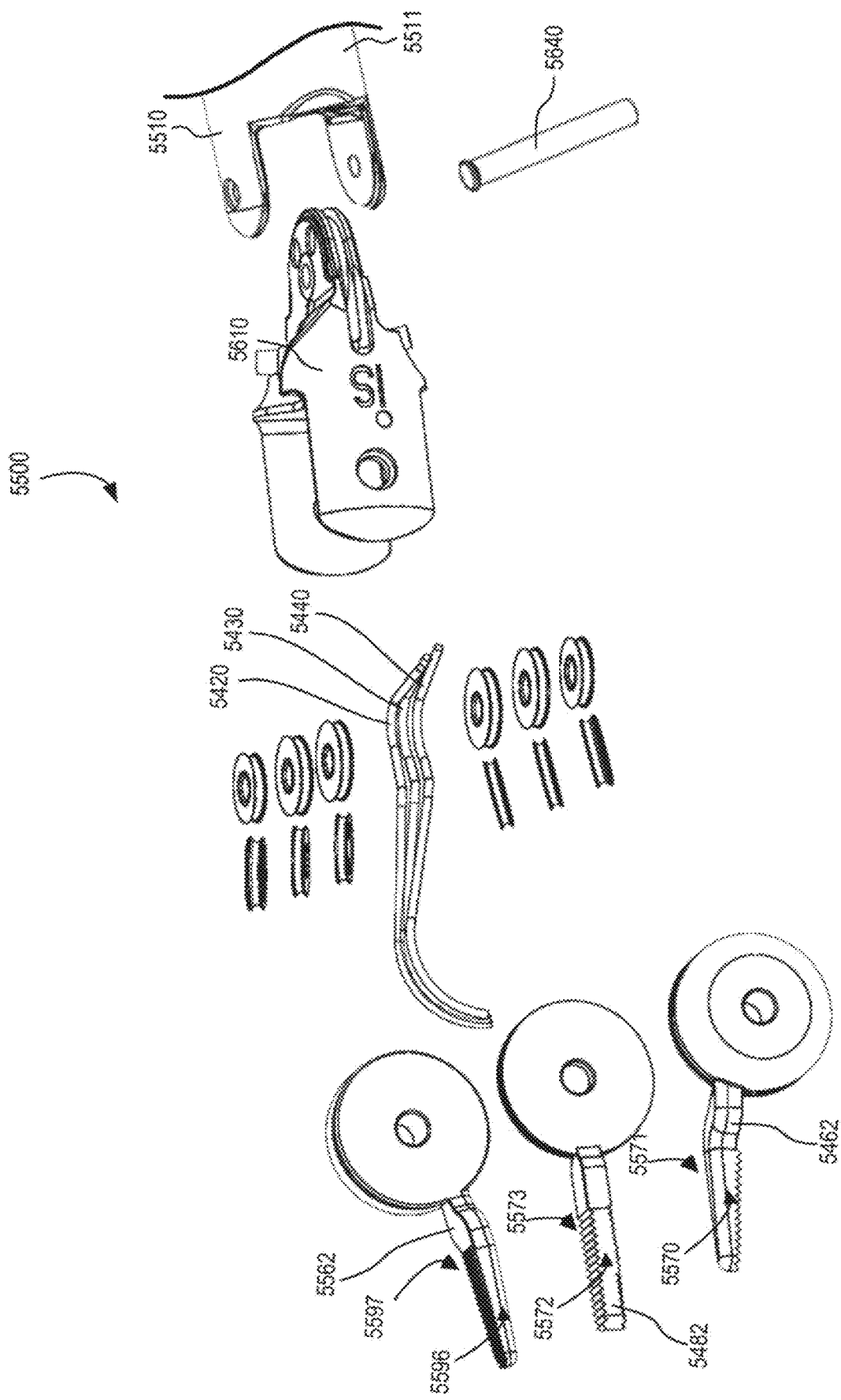
FIG. 11 is a side perspective view of the distal end portion of the instrument of FIG. 8A shown in an exploded view.
Figure 12:
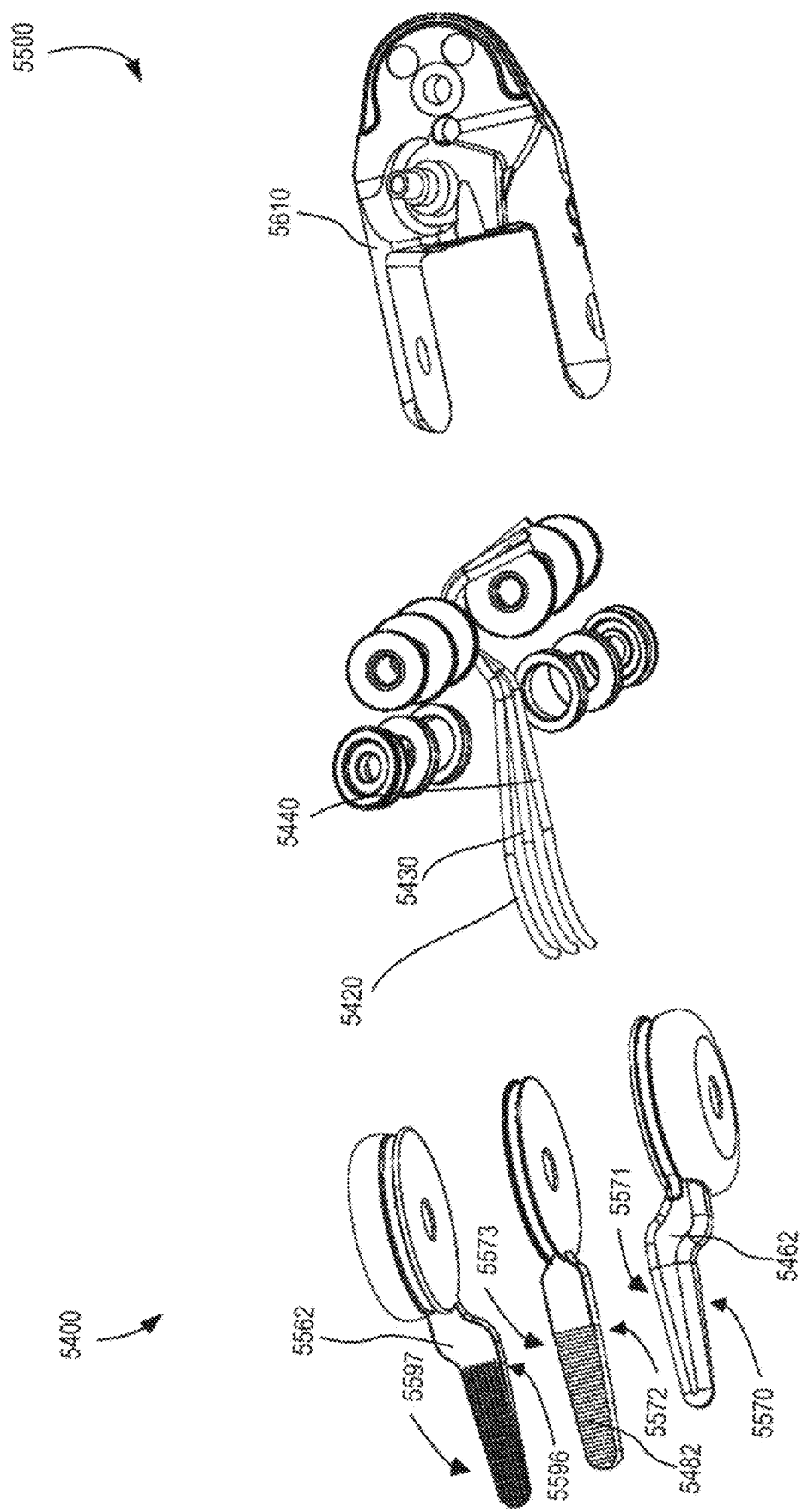
FIG. 12 is a top perspective view of the distal end portion of the instrument of FIG. 8A shown in an exploded view without showing the proximal clevis.
Figure 13:
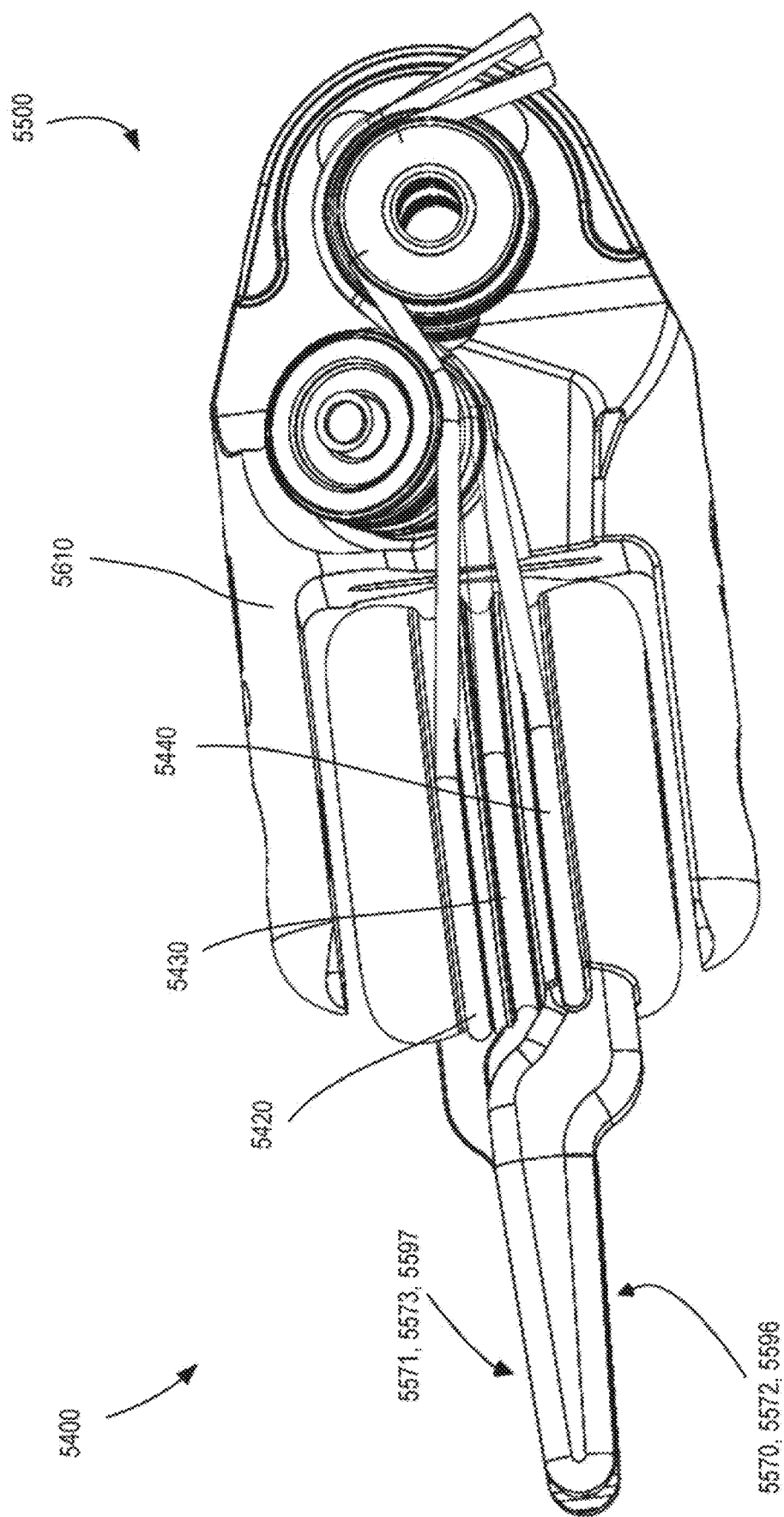
FIG. 13 is a top view of the distal end portion of the instrument of FIG. 8A.

Referring now to FIG. 10 and as discussed herein, each of the first, second and third tool members 5462, 5482 and 5562 can be configured for independent rotation with respect to distal clevis 5610 about the common axis, $A_2$. In particular, the first tool member 5462 can rotate about axis $A_2$ independent of movement the second and third tool members 5482 and 5562 the directions shown by arrow DD in FIG. 10. The second tool member 5582 can similarly rotate in the direction shown by arrow CC independent of movements of the other tool members, and the third tool member 5567 can rotate in the direction shown by arrow BB independent of movements of the other tool members. Referring now to FIG. 11, each of the first, second and third tool members are configured as elongate members in combination with their proximal pulley portion.

Thus, instrument 5400 provides many beneficial features for providing expanded functions, and options for performing clinical functions including expanded features based on its gripping-type functions including having two gripping pairs, as well as increased flexibility provided by having three independently controllable tool members. Further, instrument 5400 has been configured greatly expanded by also being configured to perform retractor-type functions.

While various embodiments have been described above, it should be understood that they have been presented by way of example only, and not limitation. Where methods and/or schematics described above indicate certain events and/or flow patterns occurring in certain order, the ordering of certain events and/or operations may be modified. While the embodiments have been particularly shown and described, it will be understood that various changes in form and details may be made.

For example, any of the instruments described herein (and the components therein) are optionally parts of a surgical assembly that performs minimally invasive surgical procedures, and which can include a patient-side cart, a series of kinematic linkages, a series of cannulas, or the like. Thus, any of the instruments described herein can be used in any suitable surgical system, such as the MIRS system 1000 shown and described above. Moreover, any of the instruments shown and described herein can be used to manipulate target tissue during a surgical procedure. Such target tissue can be cancer cells, tumor cells, lesions, vascular occlusions, thrombosis, calculi, uterine fibroids, bone metastases, adenomyosis, or any other bodily tissue. The presented examples of target tissue are not an exhaustive list. Moreover, a target structure can also include an artificial substance (or non-tissue) within or associated with a body, such as for example, a stent, a portion of an artificial tube, a fastener within the body or the like.

For example, any of the tool members can be constructed from any material, such as medical grade stainless steel, nickel alloys, titanium alloys, or the like. Further, any of the links, tool members, tension members, or components described herein can be constructed from multiple pieces that are later joined together. For example, in some embodiments, a link can be constructed by joining together separately constructed components. In other embodiments, however, any of the links, tool members, tension members, or components described herein can be monolithically constructed.

Although various embodiments have been described as having particular features and/or combinations of components, other embodiments are possible having a combination of any features and/or components from any of embodiments as discussed above. Aspects have been described in the general context of medical devices, and more specifically surgical instruments, but inventive aspects are not necessarily limited to use in medical devices.

What is claimed is:

1. An apparatus, comprising:
an instrument shaft;
a wrist assembly movable about an axis, the wrist assembly including a distal link;
a first tool member comprising a proximal end portion movably coupled to the distal link and a distal end portion configured to engage a first object;
a second tool member comprising a proximal end portion movably coupled to the distal link and a distal end portion configured to engage at least the first object or a second object;
a third tool member comprising a proximal end portion movably coupled to the distal link and a distal end portion configured to engage at least one of the first object or the second object;
a first tension member coupled to the first tool member;
a second tension member coupled to the second tool member; and
a third tension member coupled to the third tool member;
wherein:
the first, second, and third tool members are rotatable about the distal link,
the first, second, and third tension members each extend through the instrument shaft and are routed through the wrist assembly allowing for movability of the wrist assembly about the axis,
the first tool member moves relative to the distal link independent of movement of the second tool member and independent of movement of the third tool member,
the second tool member moves relative to the distal link independent of movement of the first tool member and independent of movement of the third tool member, and
the third tool member moves relative to the distal link independent of movement of the first tool member and independent of movement of the second tool member.

2. The apparatus of claim 1, wherein:
the distal link is a distal clevis of a wrist assembly; and
the distal clevis comprises a pin about which at least two of the first tool member, the second tool member, and the third tool member rotate.

3. The apparatus of claim 2, wherein:
the first tool member comprises a first elongate blade coupled to the distal clevis to rotate about the pin, the first elongate blade comprising a first contact surface;
the second tool member comprises a second elongate blade coupled to the distal clevis to rotate about the pin, the second elongate blade comprising a second contact surface; and
the third tool member comprises a third elongate blade coupled to the distal clevis to rotate about the pin, the third elongate blade comprising a third contact surface.

4. The apparatus of claim 3, wherein:
the first, second and third elongate blades are configured to rotate to an aligned orientation in which the first contact surface, the second contact surface, and the third contact surface are aligned with each other; and
the first, second and third elongate blades are configured to rotate to a second expanded orientation in which the first contact surface, the second contact surface, and the third contact surface are rotated apart from each other.

5. The apparatus of claim 4, wherein a first longitudinal axis of the first elongate blade is coaxial with a second longitudinal axis of the second elongate blade and a third longitudinal axis of the third elongate blade when the first elongate blade, the second elongate blade, and the third elongate blade are in the aligned orientation.

6. The apparatus of claim 1, wherein:
the proximal end portion of the first tool member is coupled to the first tension member, the first tool member movable relative to the distal link when the first tension member is moved, the first tension member being routed over a first pulley in the wrist assembly;
the proximal end portion of the second tool member is coupled to the second tension member, the second tool member movable relative to the distal link when the second tension member is moved, the second tension member being routed over a second pulley in the wrist assembly; and
the proximal end portion of the third tool member is coupled to the third tension member, the third tool member movable relative to the distal link when the third tension member is moved, the third tension member being routed over a third pulley in the wrist assembly.

7. The apparatus of claim 1, wherein the second tool member is between the first tool member and the third tool member.

8. The apparatus of claim 1, wherein:
the distal end portion of the first tool member has a first contact surface;
the distal end portion of the second tool member has a second contact surface and a fourth contact surface, the first contact surface and the second contact surface being configured to manipulate the first object; and
the distal end portion of the third tool member has a third contact surface, the third contact surface and the fourth contact surface being configured to manipulate the second object.

9. The apparatus of claim 8, wherein:
the first contact surface and the second contact surface have a first grip pattern;
the third contact surface and the fourth contact surface have a second grip pattern; and
the second grip pattern is different from the first grip pattern.

10. The apparatus of claim 9, wherein:
the second contact surface is on a first side of the second tool member, the first grip pattern on the first contact surface being aligned with the first grip pattern on the second contact surface when the first contact surface and the second contact surface manipulate the first object; and
the fourth contact surface is on a second side of the second tool member, the second grip pattern on the third contact surface being aligned with the second grip pattern on the fourth contact surface when the third contact surface and the fourth contact surface manipulate the second object.

11. A medical device, comprising:
a clevis assembly comprising a clevis pin;
a first jaw piece comprising a portion associated with a first medical function;
a second jaw piece comprising an obverse portion associated with the first medical function and a reverse portion associated with a second medical function; and
a third jaw piece comprising a portion associated with the second medical function;
wherein:
the first jaw piece, the second jaw piece, and the third jaw piece rotate around the clevis pin,
the portion of the first jaw piece associated with the first medical function opposes the obverse portion of the second jaw piece associated with the first medical function, and
the portion of the third jaw piece associated with the second medical function opposes the reverse portion of the second jaw piece associated with the second medical function;
wherein:
the medical device further comprises an instrument shaft, the instrument shaft comprising a distal end;
the clevis assembly is coupled to the distal end of the instrument shaft a first tension member extending through the instrument shaft, exiting the distal end of the instrument shaft and being routed through the clevis assembly and then coupling to the first jaw piece;
a second tension member extending through the instrument shaft, exiting the distal end of the instrument shaft and being routed through the clevis assembly and then coupling to the second jaw piece; and
a third tension member extending through the instrument shaft, exiting the distal end of the instrument shaft and being routed through the clevis assembly and then coupling to the third jaw piece.

12. The medical device of claim 11, wherein:
the medical device further comprises a transmission assembly, the transmission assembly comprising a plurality of drive components;
the instrument shaft comprises a proximal end;
the transmission assembly is coupled to the proximal end of the instrument shaft; and
the first, second, and third tension members are each coupled to a corresponding one of the plurality of drive components of the transmission assembly.

13. The medical device of claim 11, wherein:
the first and second jaw pieces are movably coupled such that the portion of the first jaw piece associated with the first medical function and the obverse portion of the second jaw piece associated with the first medical function close together; and
the third and second jaw pieces are movably coupled such that the portion of the third jaw piece associated with the second medical function and the reverse portion of the second jaw piece associated with the second medical function close together.

14. The medical device of claim 11, wherein:
the clevis assembly is a first clevis assembly and the clevis pin is a first clevis pin;
the medical device further comprises a second clevis assembly;
the second clevis assembly comprises a second clevis pin; and
the first clevis assembly rotates around the second clevis pin.

15. The medical device of claim 11, wherein:
a proximal end portion of the first jaw piece is coupled to the first tension member, the first jaw piece movable relative to the clevis pin when the first tension member is moved, the first tension member being routed over a first pulley in the clevis assembly;
a proximal end portion of the second jaw piece is coupled to the second tension member, the second jaw piece movable relative to the clevis pin when the second tension member is moved, the second tension member being routed over a second pulley in the clevis assembly; and
a proximal end portion of the third jaw piece is coupled to the third tension member, the third jaw piece movable relative to the clevis pin when the third tension member is moved, the third tension member being routed over a third pulley in the clevis assembly.

* * * * *

UNITED STATES PATENT AND TRADEMARK OFFICE
CERTIFICATE OF CORRECTION

PATENT NO. : 11,612,447 B2
APPLICATION NO. : 16/513105
DATED : March 28, 2023
INVENTOR(S) : Timothy A. Limon and Grant Duque It is certified that error appears in the above-identified patent and that said Letters Patent is hereby corrected as shown below:

In the Claims

Column 27, Line 59 (Claim 11): the phrase "instrument shaft" should be -- instrument shaft; --

Signed and Sealed this
Second Day of May, 2023

Katherine Kelly Vidal
*Director of the United States Patent and Trademark Office*